(12) United States Patent
Ohsawa et al.

(10) Patent No.: US 7,235,343 B2
(45) Date of Patent: Jun. 26, 2007

(54) PHOTOACID GENERATORS, CHEMICALLY AMPLIFIED RESIST COMPOSITIONS, AND PATTERNING PROCESS

(75) Inventors: Youichi Ohsawa, Niigata-ken (JP); Katsuhiro Kobayashi, Niigata-ken (JP); Tatsushi Kaneko, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 18 days.

(21) Appl. No.: 10/842,719

(22) Filed: May 11, 2004

(65) Prior Publication Data
US 2004/0229162 A1 Nov. 18, 2004

(30) Foreign Application Priority Data
May 12, 2003 (JP) ............................. 2003-132523

(51) Int. Cl.
G03F 7/031 (2006.01)
(52) U.S. Cl. .................................... 430/270.1; 430/921
(58) Field of Classification Search ..................... None
See application file for complete search history.

(56) References Cited

U.S. PATENT DOCUMENTS

| 4,120,866 | A | * | 10/1978 | Winkler ..................... 548/440 |
|---|---|---|---|---|
| 5,585,507 | A | | 12/1996 | Nakano et al. |
| 5,635,332 | A | | 6/1997 | Nakano et al. |
| 5,756,850 | A | | 5/1998 | Iwasa et al. |
| 6,004,724 | A | | 12/1999 | Yamato et al. |
| 6,093,753 | A | | 7/2000 | Takahashi |
| 6,187,504 | B1 | | 2/2001 | Suwa et al. |
| 6,261,738 | B1 | | 7/2001 | Asakura et al. |
| 6,274,286 | B1 | | 8/2001 | Hatakeyama et al. |
| 6,440,634 | B1 | | 8/2002 | Ohsawa et al. |
| 6,541,179 | B2 | | 4/2003 | Hatakeyama et al. |
| 6,602,647 | B2 | | 8/2003 | Iwasa et al. |
| 6,682,869 | B2 | | 1/2004 | Ohsawa et al. |
| 6,686,429 | B2 | * | 2/2004 | Dammel et al. ............. 526/297 |
| 2002/0098443 | A1 | | 7/2002 | Hatakeyama et al. |
| 2002/0115018 | A1 | | 8/2002 | Hatakeyama et al. |
| 2002/0172886 | A1 | | 11/2002 | Momota et al. |
| 2003/0198889 | A1 | | 10/2003 | Iwasa et al. |

FOREIGN PATENT DOCUMENTS

| GB | 2 348 644 A | 10/2000 |
|---|---|---|
| JP | 7-25846 A | 1/1995 |
| JP | 7-28237 A | 1/1995 |
| JP | 8-27102 A | 1/1996 |
| JP | 8-146607 A | 6/1996 |
| JP | 9-95479 A | 4/1997 |
| JP | 9-118663 A | 5/1997 |
| JP | 9-208554 A | 8/1997 |
| JP | 9-230588 A | 8/1997 |
| JP | 9-301948 A | 11/1997 |
| JP | 10-48814 A | 2/1998 |
| JP | 10-232490 A | 9/1998 |
| JP | 10-319581 A | 12/1998 |
| JP | 11-84639 A | 3/1999 |
| JP | 2906999 A | 4/1999 |
| JP | 11-190904 A | 7/1999 |
| JP | 2000-292917 A | 10/2000 |
| JP | 2000-314956 A | 11/2000 |
| JP | 2001-122850 A | 5/2001 |
| JP | 2001-324813 A | 11/2001 |
| JP | 2001-337448 A | 12/2001 |
| JP | 2001-354669 A | 12/2001 |
| JP | 2002-23354 A | 1/2002 |
| JP | 2002-40636 A | 2/2002 |
| JP | 2002-226470 A | 8/2002 |
| JP | 2002-229192 A | 8/2002 |
| JP | 2002-249478 A | 9/2002 |
| JP | 2002-278053 A | 9/2002 |
| JP | 2002-363146 A | 12/2002 |
| JP | 2002-363148 A | 12/2002 |
| JP | 2002-363152 A | 12/2002 |

OTHER PUBLICATIONS

Azuma et al, SPIE, 3999, 264-269 (2000).
Koji Arimitsu et al., J. Photopolym, Sci. and Tech., vol. 9, No. 1, pp. 29-30 (1996).
Koji Arimitsu et al., J. Photopolym, Sci. and Tech., vol. 8, No. 1, pp. 43-46 (1995).

* cited by examiner

*Primary Examiner*—Barbara L. Gilliam
(74) *Attorney, Agent, or Firm*—Birch, Stewart, Kolasch & Birch, LLP

(57) ABSTRACT

Photoacid generators have formula (1) wherein $R^1$ and $R^2$ are alkyl, or $R^1$ and $R^2$, taken together, may form a $C_4$–$C_6$ ring structure with sulfur, R is hydrogen or alkyl, R' is hydrogen, alkyl, alkoxyl or nitro, n is 1 to 6, and $Y^-$ is alkylsulfonate, arylsulfonate, bisalkylsulfonylimide or trisalkylsulfonylmethide. Chemically amplified resist compositions comprising the same have improved resolution, thermal stability, storage stability and minimized line edge roughness

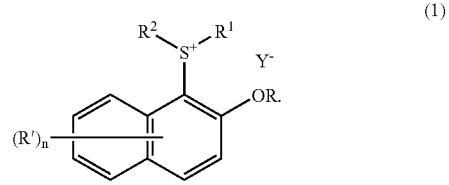

(1)

16 Claims, No Drawings

PHOTOACID GENERATORS, CHEMICALLY AMPLIFIED RESIST COMPOSITIONS, AND PATTERNING PROCESS

This Nonprovisional application claims priority under 35 U.S.C. § 119(a) on Patent Application No(s). 2003-132523 filed in JAPAN on, May 12, 2003, the entire contents of which are hereby incorporated by reference.

This invention relates to photoacid generators for chemically amplified resist compositions, chemically amplified resist compositions comprising the photoacid generators, and a patterning process using the same. The chemically amplified resist compositions are sensitive to such radiation as UV, deep UV, electron beams, x-rays, excimer laser beams, γ-rays, and synchrotron radiation and suitable for the microfabrication of integrated circuits.

BACKGROUND OF THE INVENTION

While a number of recent efforts are being made to achieve a finer pattern rule in the drive for higher integration and operating speeds in LSI devices, DUV and VUV lithography is thought to hold particular promise as the next generation in microfabrication technology. At present, the manufacture of advanced semiconductor devices having a feature size of 0.15 µm is conducted by photolithography using a KrF excimer laser, and even 0.13-µm rule devices are on the verge of commercial manufacture. It is strongly desired that photolithography using an ArF excimer laser as the light source reach the practical level as the micropatterning technique capable of achieving a feature size of 0.13 µm or less.

In the photolithography using an ArF excimer laser (wavelength 193 nm) as the light source, a high sensitivity resist material capable of achieving a high resolution at a small dose of exposure is needed to prevent the degradation of precise and expensive optical system materials. Among several measures for providing a high sensitivity resist material, the most common is to select each component which is highly transparent at the wavelength of 193 nm. For example, poly(meth)acrylic acid and derivatives thereof, norbornene-maleic anhydride alternating copolymers, polynorbornene and metathesis ring-opening polymers have been proposed as the base resin. This choice is effective in that the transparency of a resin alone is increased. However, the photoacid generator has the problem that increasing its transparency leads to a drop of acid generation efficiency, resulting in a low sensitivity or the lack of thermal stability and storage stability. There is available no photoacid generator which is practically acceptable.

For example, JP-A 7-25846, JP-A 7-28237, JP-A 8-27102, JP-A 2001-354669, and JP-A 2002-40636 disclose alkylsulfonium salts which are highly transparent, but unsatisfactory in acid generation efficiency and thermal stability. The following salts are illustrated in JP-A 7-25846, JP-A 2001-354669, and JP-A 2002-40636.

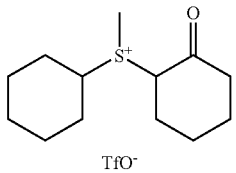

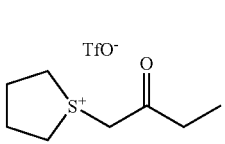

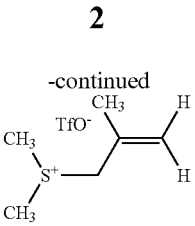

JP-A 10-319581 discloses alkylarylsulfonium salts which have a high sensitivity and a good balance of transparency and acid generation efficiency, but lack thermal stability and storage stability.

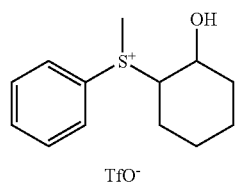

Further, JP-A 8-146607, JP-A 9-118663, JP-A 10-48814, JP-A 10-232490 and JP-A 2002-229192 disclose sulfonium salts having naphthyl groups, and describe that resist compositions comprising the same exhibit a high sensitivity, high resolution and improved pattern configuration. These naphthyl group-containing sulfonium salts have a high transmittance near 193 nm, but an inferior sensitivity to the conventional triarylsulfonium salts. The sensitivity can be enhanced by increasing the amount of the salt added to resist compositions, but noticeable demerits are introduced. That is, adding large amounts of low-molecular weight components to resist compositions can cause degradation of dissolution properties, precipitation of substantially insoluble sulfonium salts, and conversion thereof into foreign matter.

Additional drawbacks are that for example, trinaphthylsulfonium salts and 2-dialkylnaphthylsulfonium salts are difficult to produce, and that 1-naphthyldialkylsulfonium salts which are unsubstituted (hydrogen atom) at 2-position lack storage stability in resist solution.

The following salts are disclosed in JP-A 8-146607, JP-A 9-118663, JP-A 10-48814, JP-A 10-232490 and JP-A 2002-229192.

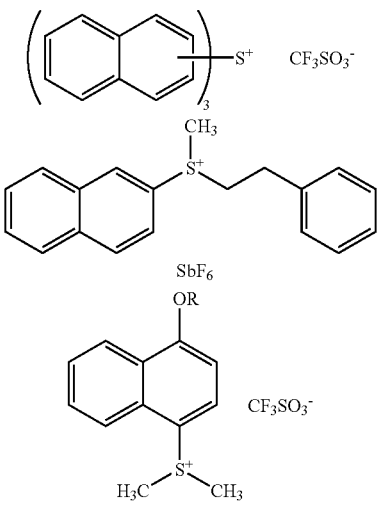

-continued

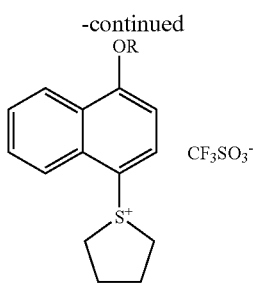

Arylsulfonium salts, which are regarded effective in photolithography using a KrF excimer laser, are good in acid generation efficiency, thermal stability and storage stability, but very low transparent to light so that the pattern resulting from exposure and development is noticeably tapered. The lack of transparency can be compensated for by thinning the resist film, but such a thin resist film has extremely low etch resistance. This is inadequate as the pattern forming process. Most of the foregoing salts are onium salts whose cation side structure is modified. It was reported that with respect to resolution and pattern configuration, there is a close relationship between the type of acid generated and the type of acid labile group.

With the advance toward a finer feature size, line edge roughness and a size difference between an isolated pattern and a densely packed pattern, known as I/G bias are regarded problematic. It is well known that even when feature sizes are the same on the mask, a size difference appears between an isolated pattern and a densely packed pattern after development. This problem becomes serious with sizes in excess of the wavelength. This is because a difference in light interference upon image formation between an isolated pattern and a densely packed pattern brings about a difference in optical intensity. The resist size decreases with an increase of pitch (pitch=the sum of line size and space size, in this case, the line size remains unchanged and the space size is increased) and becomes increasingly thinner with the enhancement of acid diffusion. The problem of size dependency on line density that the size of an isolated pattern is thinner than that of a densely packed pattern becomes serious. One proposed approach for reducing the line density dependency is to reduce the distance of acid diffusion. However, if acid diffusion is extremely restrained, the side walls of resist patterns after development are serrated or roughened by standing waves, and line edge roughness is enhanced. It has been reported that the serration of side walls by standing waves becomes sharper as the distance of acid diffusion is reduced. For the line edge roughness as observed under top-down SEM, the same tendency is ascertained, that is, line edge roughness increases as acid diffusion decreases. A common approach for reducing the roughness of lines is by increasing the distance of acid diffusion, but this approach fails to improve the line density dependency over a certain limit. For improving line edge roughness, it may be effective to increase the optical contrast. For example, at the same exposure wavelength, the line edge roughness decreases as the line width increases. Even at the same exposure wavelength and line width, the line edge roughness decreases with an increasing NA of a stepper and in the case of repetitive patterns, is smaller with modified illumination (e.g., annular illumination, quadrupole illumination) than with normal illumination and with phase shift masks than with conventional Cr masks. The contrast at pattern line edges is correlated to the line edge roughness so that the line edge roughness becomes smaller as the line edge contrast becomes sharper. With respect to exposure wavelength, it is expected that the line edge roughness becomes smaller upon exposure at shorter wavelengths. However, when line edge roughness is compared between KrF exposure and ArF exposure, the ArF exposure is deemed to provide a higher optical contrast owing to its shortness of wavelength and a smaller line edge roughness, but actually, the KrF exposure is advantageous, as reported in SPIE 3999, 264 (2000). This is attributable to the performance difference between KrF and ArF resist materials, indicating that the line edge roughness originating from material factors upon ArF exposure is serious. It would be desirable to have a photoacid generator which improves line edge roughness and at the same time, does not exacerbate line density dependency.

SUMMARY OF THE INVENTION

The photoacid generators for use in resist compositions are required to have a fully high solubility (or compatibility) in resist solvents and resins, good storage stability, non-toxicity, ease of application, good pattern profile shape, PED stability, high resolution and especially, good sensitivity, and ease of synthesis. Conventional photoacid generators, especially alkylsulfonium compound photoacid generators fail to satisfy all of these requirements.

An object of the invention is to provide a photoacid generator which is easy to synthesize and affords a chemically amplified resist composition having a high sensitivity and high resolution, a resist composition comprising the same, and a patterning process using the resist composition.

It has been found that a resist composition comprising a photoacid generator in the form of a sulfonium salt having the formula (1) defined below, especially a sulfonium salt having the formula (1a) or (1b), is improved in dissolution, storage stability, and ease of application, experiences minimized line width changes and shape degradation even in the case of long lasting PED, affords an improved pattern profile shape following development, and exhibits a high resolution and sensitivity suited for micropatterning, especially by deep-UV lithography.

In a first aspect, the present invention provides a photoacid generator for chemically amplified resist compositions, having the following general formula (1).

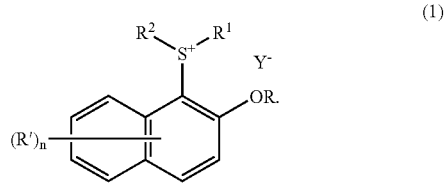

Herein $R^1$ and $R^2$ are each independently a straight, branched or cyclic, unsubstituted or oxygen-containing alkyl group of 1 to 6 carbon atoms, or $R^1$ and $R^2$, taken together, may form an unsubstituted or oxygen-containing ring structure of 4 to 6 carbon atoms with the sulfur atom to which they are attached; R is hydrogen or a substituted or unsubstituted alkyl group of 1 to 10 carbon atoms; R' is hydrogen, a substituted or unsubstituted alkyl group of 1 to 10 carbon atoms, a substituted or unsubstituted alkoxyl group of 1 to 10 carbon atoms, or a nitro group; n is an integer of 1 to 6; and $Y^-$ is a substituted or unsubstituted alkylsulfonate of 1 to 10 carbon atoms, a substituted or unsubstituted arylsulfonate of 6 to 20 carbon atoms, a substituted or unsubstituted bisalkylsulfonylimide of 2 to 10 carbon atoms, or a substituted or unsubstituted trisalkylsulfonylmethide of 3 to 12 carbon atoms.

Another embodiment is a photoacid generator for chemically amplified resist compositions, having the following general formula (1a).

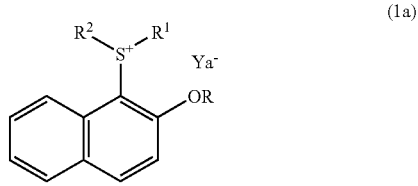

(1a)

Herein $R^1$ and $R^2$ are each independently a straight, branched or cyclic, unsubstituted or oxygen-containing alkyl group of 1 to 6 carbon atoms, or $R^1$ and $R^2$, taken together, may form an unsubstituted or oxygen-containing ring structure of 4 to 6 carbon atoms with the sulfur atom to which they are attached; R is hydrogen or a substituted or unsubstituted alkyl group of 1 to 10 carbon atoms; and $Ya^-$ is a perfluoroalkylsulfonate of 1 to 8 carbon atoms, bis(perfluoroalkylsulfonyl)imide of 2 to 10 carbon atoms or tris(perfluoroalkylsulfonyl)methide of 3 to 12 carbon atoms.

A further embodiment is a photoacid generator for chemically amplified resist compositions, having the following general formula (1b).

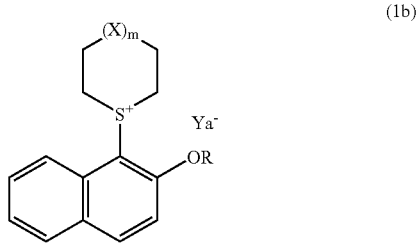

(1b)

Herein R is hydrogen or a substituted or unsubstituted alkyl group of 1 to 10 carbon atoms; $Ya^-$ is a perfluoroalkylsulfonate of 1 to 8 carbon atoms, bis(perfluoroalkylsulfonyl)imide of 2 to 10 carbon atoms or tris(perfluoroalkylsulfonyl)methide of 3 to 12 carbon atoms; X is $CH_2$ (methylene) or O (oxygen atom); and m is 0 or 1.

In a second aspect, the invention provides a chemically amplified resist composition comprising (A) a resin which changes its solubility in an alkaline developer under the action of an acid, and (B) the photoacid generator defined above.

A preferred embodiment is a chemically amplified positive resist composition comprising (A) a resin which changes its solubility in an alkaline developer under the action of an acid, and (B) the photoacid generator defined above. The resist composition may further comprise (C) a compound capable of generating an acid upon exposure to radiation, other than component (B) and desirably, (D) a basic compound. In a preferred embodiment, the resin (A) has such substituent groups having C—O—C linkages that the solubility in an alkaline developer changes as a result of scission of the C—O—C linkages under the action of an acid.

In a third aspect, the invention provides a process for forming a pattern, comprising the steps of (i) applying the resist composition onto a substrate to form a coating, (ii) heat treating the coating and exposing the coating to high energy radiation with a wavelength of up to 250 nm or electron beam through a photomask, (iii) optionally heat treating the exposed coating, and developing the coating with a developer.

DESCRIPTION OF THE PREFERRED EMBODIMENTS

Photoacid Generator

In the first aspect, the present invention provides photoacid generators for use in chemically amplified resist compositions, represented by the general formulae (1), (1a) and (1b).

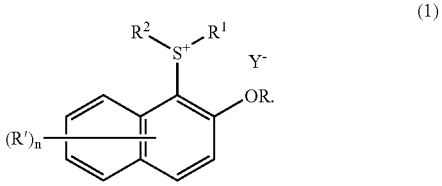

(1)

In formula (1), $R^1$ and $R^2$, which may be the same or different, are each independently a straight, branched or cyclic, unsubstituted or oxygen-containing alkyl group of 1 to 6 carbon atoms, or $R^1$ and $R^2$, taken together, may form an unsubstituted or oxygen-containing ring structure of 4 to 6 carbon atoms with the sulfur atom to which they are attached. R is hydrogen or a substituted or unsubstituted alkyl group of 1 to 10 carbon atoms. R' is hydrogen, a substituted or unsubstituted alkyl group of 1 to 10 carbon atoms, a substituted or unsubstituted alkoxyl group of 1 to 10 carbon atoms, or a nitro group. The subscript n is an integer of 1 to 6. $Y^-$ is a substituted or unsubstituted alkylsulfonate of 1 to 10 carbon atoms, a substituted or unsubstituted arylsulfonate of 6 to 20 carbon atoms, a substituted or unsubstituted bisalkylsulfonylimide of 2 to 10 carbon atoms, or a substituted or unsubstituted trisalkylsulfonylmethide of 3 to 12 carbon atoms.

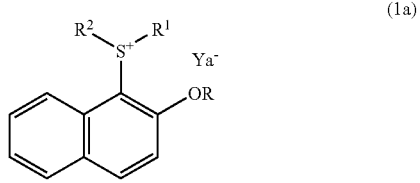

(1a)

In formula (1a), $R^1$, $R^2$ and R are as defined above. $Ya^-$ is a perfluoroalkylsulfonate of 1 to 8 carbon atoms, bis (perfluoroalkylsulfonyl)imide of 2 to 10 carbon atoms or tris(perfluoroalkylsulfonyl)methide of 3 to 12 carbon atoms.

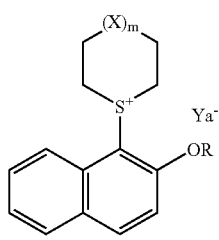

(1b)

In formula (1b), R and Ya⁻ are as defined above, X is $CH_2$ (methylene) or O (oxygen atom), and m is 0 or 1.

In formulae (1) and (1a), $R^1$ and $R^2$, which may be the same or different, are each independently a straight, branched or cyclic, unsubstituted or oxygen-containing alkyl group of 1 to 6 carbon atoms, or $R^1$ and $R^2$, taken together, may form an unsubstituted or oxygen-containing ring structure of 4 to 6 carbon atoms with the sulfur atom to which they are attached. Specifically, alkyl groups include methyl, ethyl, n-propyl, sec-propyl, n-butyl, sec-butyl, iso-butyl, tert-butyl, and n-hexyl, or $R^1$ and $R^2$ may bond together to form butylene, pentylene or 2,5-hexylene. Preferably, $R^1$ and $R^2$ are methyl or ethyl, or $R^1$ and $R^2$ bond together to form butylene.

In formulae (1), (1a) and (1b), R is hydrogen or a substituted or unsubstituted alkyl group of 1 to 10 carbon atoms. Exemplary alkyl groups include methyl, ethyl, n-propyl, sec-propyl, n-butyl, sec-butyl, iso-butyl, tert-butyl, n-pentyl, n-hexyl, cyclohexyl, and n-octyl. Of these, n-butyl, n-hexyl and cyclohexyl are preferred.

In formula (1), R' is hydrogen, a substituted or unsubstituted alkyl group of 1 to 10 carbon atoms, a substituted or unsubstituted alkoxyl group of 1 to 10 carbon atoms, or a nitro group. Exemplary alkyl groups include methyl, ethyl, n-propyl, sec-propyl, n-butyl, sec-butyl, iso-butyl, tert-butyl, n-pentyl, n-hexyl, and cyclohexyl. Exemplary alkoxyl groups include methoxy, ethoxy, n-butoxy, n-hexyloxy, and cyclohexyloxy. Of these, hydrogen, methyl and methoxy are preferred.

The subscript n is an integer of 1 to 6, and preferably an integer of 1 to 3 when R' directly attached to the naphthalene ring is other than hydrogen.

Y⁻ is a substituted or unsubstituted alkylsulfonate of 1 to 10 carbon atoms, a substituted or unsubstituted arylsulfonate of 6 to 20 carbon atoms, a substituted or unsubstituted bisalkylsulfonylimide of 2 to 10 carbon atoms, or a substituted or unsubstituted trisalkylsulfonylmethide of 3 to 12 carbon atoms. Illustrative examples include trifluoromethanesulfonate, nonafluorobutanesulfonate, heptadecafluorooctanesulfonate, perfluoro-4-ethylcyclohexanesulfonate, 2,2,2-trifluoroethanesulfonate, perfluoro-2-ethoxyethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4'-toluenesulfonyloxy)benzenesulfonate, 6-(4-toluenesulfonyloxy)naphthalene-2-sulfonate, 4-(4-toluenesulfonyloxy)naphthalene-1-sulfonate, 5-(4-toluenesulfonyloxy)naphthalene-1-sulfonate, 8-(4-toluenesulfonyloxy)naphthalene-1-sulfonate, naphthalenesulfonate, camphorsulfonate, octanesulfonate, dodecylbenzenesulfonate, butanesulfonate, methanesulfonate, bis(trifluoromethanesulfonyl)imide, bis(perfluoroethanesulfonyl)imide, bis(perfluorobutanesulfonyl)imide, tris(trifluoromethanesulfonyl)methide, and tris(perfluoroethanesulfonyl)methide.

In formulae (1a) and (1b), Ya⁻ is a perfluoroalkylsulfonate of 1 to 8 carbon atoms, bis(perfluoroalkylsulfonyl)imide of 2 to 10 carbon atoms or tris(perfluoroalkylsulfonyl)methide of 3 to 12 carbon atoms, for example, trifluoromethanesulfonate, perfluorobutanesulfonate, perfluorooctanesulfonate, perfluoro-4-ethylcyclohexanesulfonate, bis(trifluoromethanesulfonyl)imide, bis(perfluoroethanesulfonyl)imide, bis(perfluorobutanesulfonyl)imide, tris(trifluoromethanesulfonyl)methide, tris(perfluoroethanesulfonyl)methide, and tris(perfluorobutanesulfonyl)methide.

In formula (1b), X is $CH_2$ (methylene) or O (oxygen atom), and m is 0 or 1.

Shown below are illustrative examples of suitable cation skeletons of the sulfonium salts having formulae (1), (1a) and (1b).

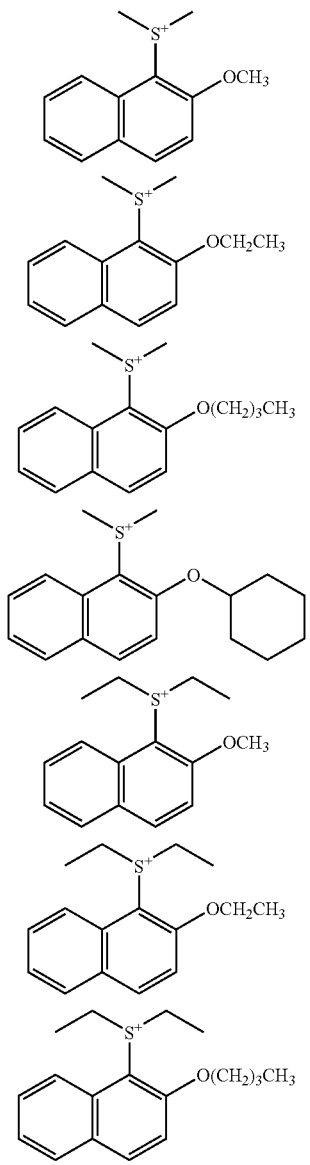

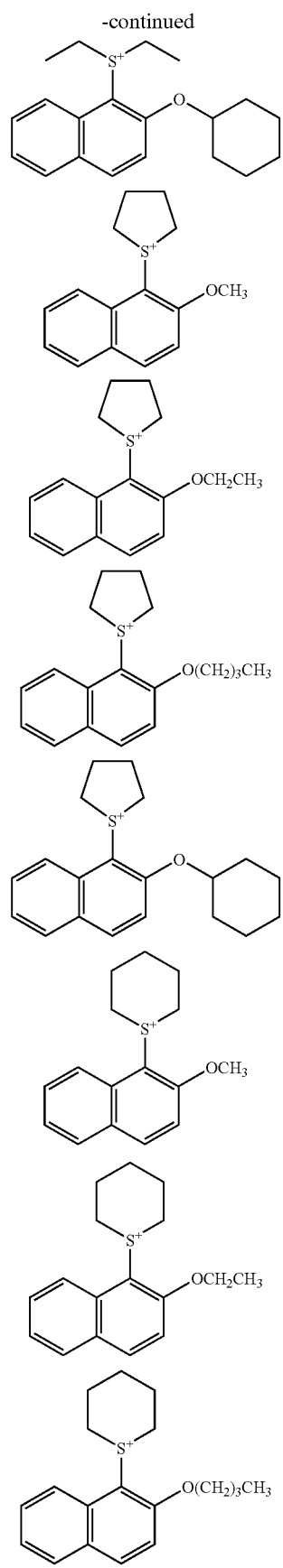

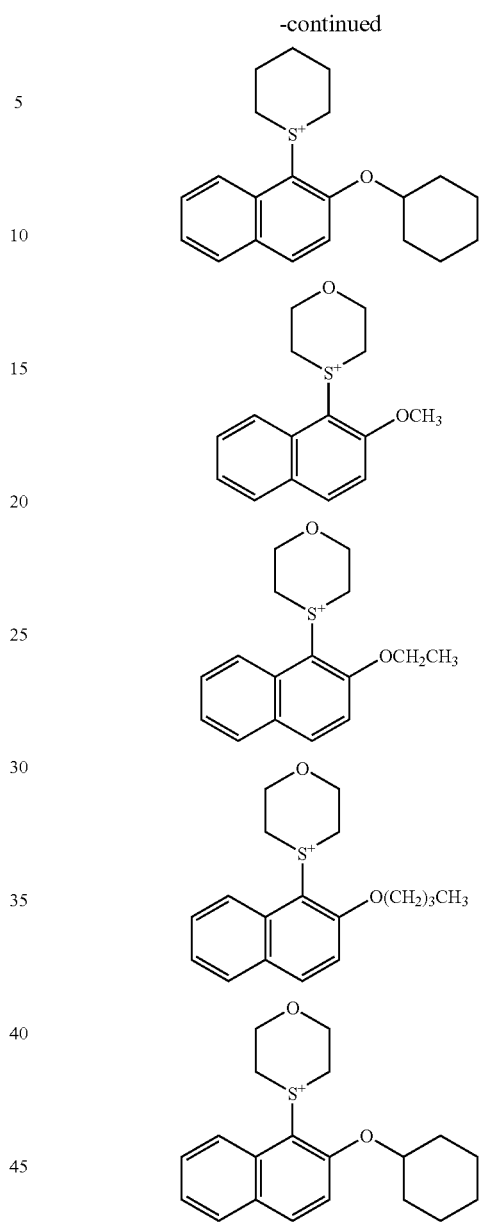

The preferred sulfonium salts of the invention are combinations of the aforementioned cations with the aforementioned anions, typically sulfonate, bisalkylsulfonylimide and trisalkylsulfonylmethide, thought not limited thereto.

Any of the existing processes may be employed for the synthesis of the sulfonium salts of the invention. For example, synthesis is made by reaction of a 2-alkoxynaphthalene with a dialkyl sulfoxide or alkylene sulfoxide according the following scheme.

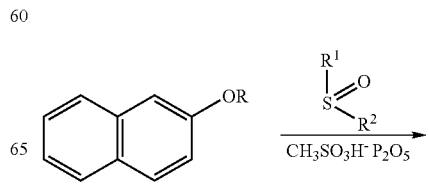

-continued

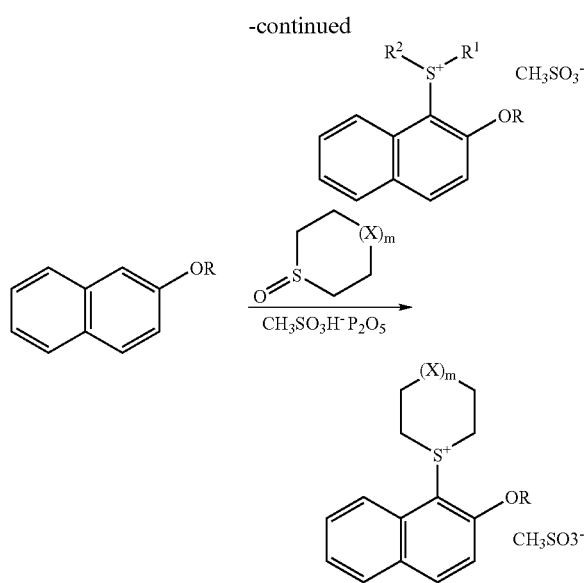

(R¹, R², R, X and m are as defined above.)

Preferably reaction of a 2-alkoxynaphthalene with a dialkyl sulfoxide or alkylene sulfoxide is carried out in the presence of a catalyst such as diphosphorus pentoxide-methanesulfonic acid. Specific catalysts include a 10 wt % solution of diphosphorus pentoxide-methanesulfonic acid, commercially available reagents such as Eaton's reagent by Aldrich, perfluoroalkylsulfonic acids, perfluoroalkylsulfonic acid anhydrides, hydrogen fluoride, aluminum chloride, and phosphoric acid.

Examples of 2-alkoxynaphthalenes include 2-methoxynaphthalene, 2-ethoxynaphthalene, 2-n-butoxynaphthalene, 2-n-hexyloxynaphthalene, and 2-cyclohexyloxynaphthalene.

Examples of dialkyl sulfoxides and alkylene sulfoxides include dimethyl sulfoxide, diethyl sulfoxide, di-n-butyl sulfoxide, di-n-hexyl sulfoxide, tetramethylene sulfoxide, pentamethylene sulfoxide, 2,5-hexylene sulfoxide and the compound shown below. Of these, tetramethylene sulfoxide is most preferred.

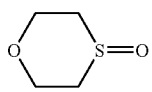

The above reaction leads to substitution of a sulfonium group at various positions on 2-alkoxynaphthalene although the main product is a compound having a sulfonium group substituted at 1-position relative to the 2-alkoxy group.

When unsubstituted naphthalene free of an electron donative group such as alkoxyl group is used, it is difficult to produce a sulfonium salt through reaction with sulfoxide. Even if possible, selectivity is often low in that the product is a mixture of 1- and 2-substituted compounds (the substitution position is the bonding position to the sulfur atom of sulfonium).

The sulfonium methanesulfonate or sulfonium having another anion resulting from the above reaction is subjected to anion exchange in an ordinary manner for conversion to the compound (1), (1a) or (1b) having Y⁻ or Ya⁻. For example, the sulfonium salt and an acid, ammonium salt or alkali metal salt of Y⁻ or Ya⁻ are mixed in an aqueous solution, after which the product precipitates. Alternatively, the sulfonium salt and an acid, ammonium salt or alkali metal salt of Y⁻ or Ya⁻ are mixed in an aqueous solution, after which the product is extracted with an organic solvent such as dichloromethane or ethyl acetate.

Resist Compositions

In the second aspect, the present invention provides a chemically amplified resist composition comprising a photoacid generator having the formula (1), (1a) or (1b). Specifically, the invention provides:

[I] a chemically amplified resist composition comprising
  (A) a resin which changes its solubility in an alkaline developer under the action of an acid, and
  (B) the aforementioned photoacid generator;
[II] a chemically amplified positive resist composition comprising
  (A) a resin which changes its solubility in an alkaline developer under the action of an acid, and
  (B) the aforementioned photoacid generator;
[III] the above resist composition further comprising (C) a compound capable of generating an acid upon exposure to radiation, other than component (B);
[IV] the above resist composition wherein the resin (A) has such substituent groups having C—O—C linkages that the solubility in an alkaline developer changes as a result of scission of the C—O—C linkages under the action of an acid; and
[V] the above resist composition further comprising (D) a basic compound.

In the third aspect, the present invention provides a process for forming a pattern, comprising the steps of (i) applying the resist composition onto a substrate to form a coating; (ii) heat treating the coating and exposing the coating to high energy radiation with a wavelength of up to 250 nm or electron beam through a photomask; (iii) optionally heat treating the exposed coating, and developing the coating with a developer.

The chemically amplified resist compositions comprising the inventive photoacid generators may be either of positive type or of negative type. Positive working resist compositions are preferred from the resolution standpoint. The resist compositions of the invention include a variety of embodiments:

<1> a chemically amplified positive working resist composition comprising (A) a resin which changes its solubility in an alkaline developer under the action of an acid, (B) the photoacid generator of formula (1), (1a) or (1b), and (F) an organic solvent;

<2> a chemically amplified positive working resist composition of <1> further comprising (C) a photoacid generator capable of generating an acid upon exposure to radiation, other than component (B);

<3> a chemically amplified positive working resist composition of <1> or <2> further comprising (D) a basic compound;

<4> a chemically amplified positive working resist composition of <1> to <3> further comprising (E) an organic acid derivative;

<5> a chemically amplified positive working resist composition of <1> to <4> further comprising (G) a compound with a molecular weight of up to 3,000 which changes its solubility in an alkaline developer under the action of an acid;

<6> a chemically amplified negative working resist composition comprising (B) the photoacid generator of formula (1), (1a) or (1b), (F) an organic solvent, (H) an alkali-soluble resin, and (I) an acid crosslinking agent capable of forming a crosslinked structure under the action of an acid;

<7> a chemically amplified negative working resist composition of <6> further comprising (C) another photoacid generator; and <8> a chemically amplified negative working resist composition of <6> or <7> further comprising (D) a basic compound.

Now the respective components are described in detail.

Component (A)

Component (A) is a resin which changes its solubility in an alkaline developer solution under the action of an acid. It is preferably, though not limited thereto, a resin having carboxyl groups in which some or all of the hydrogen atoms of carboxyl groups are protected with acid-labile groups (i.e., protective groups which are labile to acid). A resin having phenolic hydroxyl groups in which some or all of the hydroxyl groups are protected with acid-labile groups is also useful. The latter is acceptable for KrF excimer laser exposure, but unacceptable for ArF excimer laser exposure because it forms a resist film with too low a transmittance.

The base resins having acid labile groups or protective groups which are eliminated under the action of acid include polyhydroxystyrene (PHS), and copolymers of PHS with styrene, (meth)acrylic acid esters or maleimide-N-carboxylic acid esters, for KrF excimer laser resist use; (meth)acrylic acid esters, alternating copolymers of norbornene with maleic anhydride, alternating copolymers of tetracyclododecene with maleic anhydride, polynorbornene and metathesis polymerized products by ring-opening polymerization, for ArF excimer laser resist use, although the base resins are not limited to these polymers.

For polyhydroxystyrene-base resins, reference is made to JP-A 2001-122850 and JP-A 2001-324813. For carboxylic acid-base resins having low or no hydroxystyrene contents, reference is made to JP-A 2001-337448 and JP-A 2002-23354 as well as the above-cited JP-A 7-25846, JP-A 7-28237, JP-A 8-27102, JP-A 2001-354669, JP-A 2002-40636, JP-A 10-319581, and JP-A 2000-292917.

In the embodiment wherein alkali-soluble resins have phenolic hydroxyl and/or carboxyl groups in which some or all of the phenolic hydroxyl and/or carboxyl groups are protected with acid-labile substituent groups having a C—O—C linkage, the acid labile groups are selected from a variety of such groups. The preferred acid labile groups are groups of the following general formulae (4) to (7), tertiary alkyl groups of 4 to 20 carbon atoms, preferably 4 to 15 carbon atoms, trialkylsilyl groups whose alkyl groups each have 1 to 6 carbon atoms, oxoalkyl groups of 4 to 20 carbon atoms, or aryl-substituted alkyl groups of 7 to 20 carbon atoms.

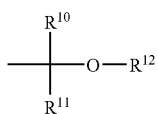

(4)

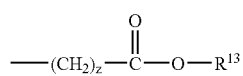

(5)

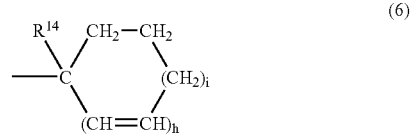

(6)

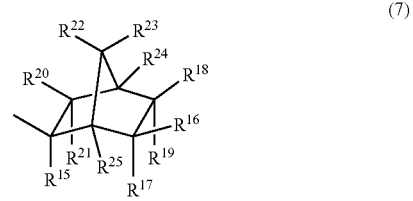

(7)

Herein $R^{10}$ and $R^{11}$ are independently hydrogen or straight, branched or cyclic alkyl groups of 1 to 18 carbon atoms, preferably 1 to 10 carbon atoms, for example, methyl, ethyl, propyl, isopropyl, n-butyl, sec-butyl, tert-butyl, cyclopentyl, cyclohexyl, 2-ethylhexyl and n-octyl. $R^{12}$ is a monovalent hydrocarbon group of 1 to 18 carbon atoms, preferably 1 to 10 carbon atoms, which may have a hetero atom (e.g., oxygen atom), for example, straight, branched or cyclic alkyl groups, and such groups in which some hydrogen atoms are substituted with hydroxyl, alkoxy, oxo, amino or alkylamino groups. Illustrative examples of the substituted alkyl groups are given below.

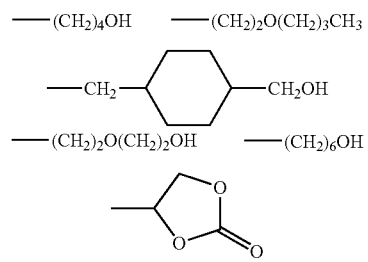

A pair of $R^{10}$ and $R^{11}$, a pair of $R^{10}$ and $R^{12}$, or a pair of $R^{11}$ and $R^{12}$, taken together, may form a ring. Each of $R^{10}$, $R^{11}$ and $R^{12}$ is a straight or branched alkylene group of 1 to 18 carbon atoms, preferably 1 to 10 carbon atoms, when they form a ring.

$R^{13}$ is a tertiary alkyl group of 4 to 20 carbon atoms, preferably 4 to 15 carbon atoms, a trialkylsilyl group whose alkyl groups each have 1 to 6 carbon atoms, an oxoalkyl group of 4 to 20 carbon atoms or a group of formula (4). Exemplary tertiary alkyl groups are tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl and 1-adamantyl-1-methylethyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-5-oxooxolan-4-yl. Letter z is an integer of 0 to 6.

$R^{14}$ is a straight, branched or cyclic alkyl group of 1 to 8 carbon atoms or substituted or unsubstituted aryl group of 6 to 20 carbon atoms. Exemplary straight, branched or cyclic alkyl groups include methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl and cyclohexylethyl. Exemplary substituted or unsubstituted aryl groups include phenyl, methylphenyl, naphthyl, anthryl, phenanthryl, and pyrenyl. Letter h is equal to 0 or 1, i is equal to 0, 1, 2 or 3, satisfying 2h+i=2 or 3.

$R^{15}$ is a straight, branched or cyclic alkyl group of 1 to 8 carbon atoms or substituted or unsubstituted aryl group of 6 to 20 carbon atoms, examples of which are as exemplified for $R^{14}$. $R^{16}$ to $R^{25}$ are independently hydrogen or monovalent hydrocarbon groups of 1 to 15 carbon atoms which may contain a hetero atom, for example, straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, and cyclohexylbutyl, and substituted forms of these groups in which some hydrogen atoms are substituted with hydroxyl, alkoxy, carboxy, alkoxycarbonyl, oxo, amino, alkylamino, cyano, mercapto, alkylthio, and sulfo groups. $R^{16}$ to $R^{25}$, for example, a pair of $R^{16}$ and $R^{17}$, a pair of $R^{16}$ and $R^{18}$, a pair of $R^{17}$ and $R^{19}$, a pair of $R^{18}$ and $R^{19}$, a pair of $R^{20}$ and $R^{21}$, or a pair of $R^{22}$ and $R^{23}$, taken together, may form a ring. When $R^{16}$ to $R^{25}$ form a ring, they are divalent hydrocarbon groups of 1 to 15 carbon atoms which may contain a hetero atom, examples of which are the above-exemplified monovalent hydrocarbon groups with one hydrogen atom eliminated. Also, two of $R^{16}$ to $R^{25}$ which are attached to adjacent carbon atoms (for example, a pair of $R^{16}$ and $R^{18}$, a pair of $R^{18}$ and $R^{24}$ or a pair of $R^{22}$ and $R^{24}$) may directly bond together to form a double bond.

Of the acid labile groups of formula (4), illustrative examples of the straight or branched groups are given below.

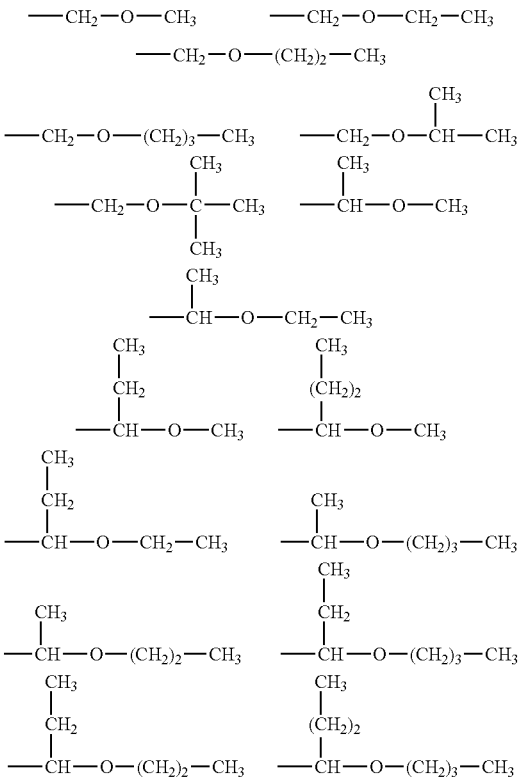

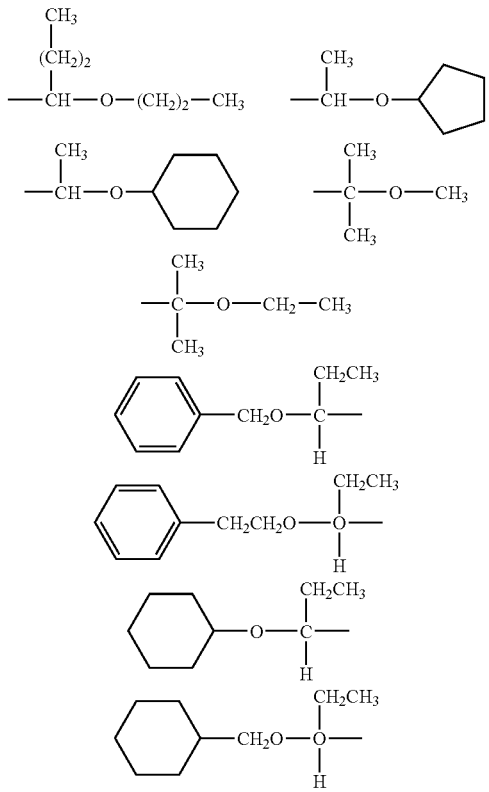

Of the acid labile groups of formula (4), illustrative examples of the cyclic groups include tetrahydrofuran-2-yl, 2-methyltetrahydrofuran-2-yl, tetrahydropyran-2-yl and 2-methyltetrahydropyran-2-yl.

Illustrative examples of the acid labile groups of formula (5) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Illustrative examples of the acid labile groups of formula (6) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, 3-ethyl-1-cyclohexen-3-yl, and 1-cyclohexyl-cyclopentyl.

Illustrative examples of the acid labile groups of formula (7) are given below.

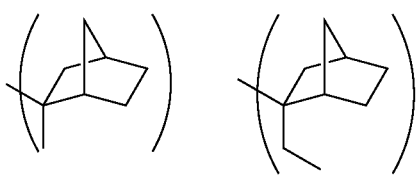

-continued

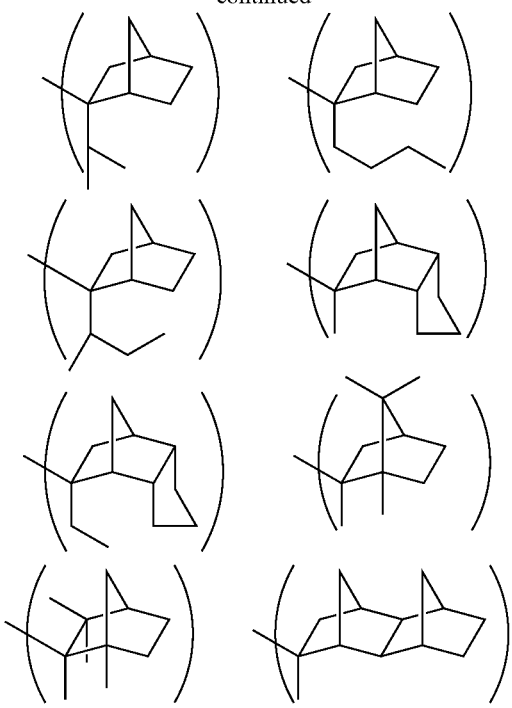

Exemplary of the tertiary alkyl group of 4 to 20 carbon atoms, preferably 4 to 15 carbon atoms, are tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl, 1-adamantyl-1-methylethyl, and dimethylbenzyl.

Exemplary of the trialkylsilyl groups whose alkyl groups each have 1 to 6 carbon atoms are trimethylsilyl, triethylsilyl, and tert-butyldimethylsilyl.

Exemplary of the oxoalkyl groups of 4 to 20 carbon atoms are 3-oxocyclohexyl and groups represented by the following formulae.

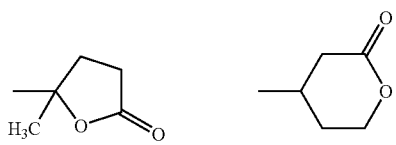

Exemplary of the aryl-substituted alkyl groups of 7 to 20 carbon atoms are benzyl, methylbenzyl, dimethylbenzyl, diphenylmethyl, and 1,1-diphenylethyl.

Also useful are resins in which some phenolic hydroxyl groups are crosslinked within a molecule and/or between molecules with acid-decomposable crosslinking groups in addition to the aforementioned acid labile groups. With respect to illustrative examples and synthesis of polymers crosslinked with acid labile groups, reference should be made to JP-A 11-190904.

The foregoing polymers may be used alone or in admixture of two or more. By the use of two or more types of polymers, the characteristics of a resist composition can be adjusted. A mixture of two or more types of polymers having different molecular weights or dispersity indexes may be used.

In the resist composition of the invention, the above-described resin is added in any desired amount, and usually 65 to 99 parts by weight, preferably 65 to 98 parts by weight per 100 parts by weight of the solids in the composition. The term "solids" is used to encompass all components in the resist composition excluding the solvent. In this context, for example, 65 pbw of the resin per 100 pbw of the solids means that the resin which is solid accounts for 65 wt % of the solids.

Component (B)

Component (B) in the resist composition is the photoacid generator having formula (1), (1a) or (1b) defined above. An appropriate amount of the photoacid generator added is from 0.1 part to 10 parts by weight, and preferably from 1 to 5 parts by weight, per 100 parts by weight of the solids in the composition.

Component (C)

In one preferred embodiment, the resist composition further contains (C) a compound capable of generating an acid upon exposure to high-energy radiation (UV, deep UV, electron beams, x-rays, excimer laser beams, gamma-rays or synchrotron radiation), that is, a second photoacid generator other than component (B). Suitable second photoacid generators include sulfonium salts, iodonium salts, sulfonyldiazomethane, N-sulfonyloxydicarboxyimide, O-arylsulfonyloxime and O-alkylsulfonyloxime photoacid generators. Exemplary second photoacid generators are given below while they may be used alone or in admixture of two or more.

Sulfonium salts are salts of sulfonium cations with sulfonates. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 4-methylphenyldiphenylsulfonium, 4-tert-butylphenyldiphenylsulfonium, bis(4-tert-butylphenyl)phenylsulfonium, tris(4-methylphenyl)sulfonium, tris(4-tert-butylphenyl)sulfonium, tris(phenylmethyl)sulfonium, 2-naphthyldiphenylsulfonium, dimethyl-2-naphthylsulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxopropylthiacyclopentanium, 2-oxobutylthiacyclopentanium, and 2-oxo-2-phenylethylthiacyclopentanium. Exemplary sulfonates include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4'-toluenesulfonyloxy)benzenesulfonate, 6-(4-toluenesulfonyloxy)naphthalene-2-sulfonate, 4-(4-toluenesulfonyloxy)naphthalene-1-sulfonate, 5-(4-toluenesulfonyloxy)naphthalene-1-sulfonate, 8-(4-toluenesulfonyloxy)naphthalene-1-sulfonate, naphthalenesulfonate, camphorsulfonate, octanesulfonate, dodecylbenzenesulfonate, butanesulfonate, methanesulfonate, bis(trifluoromethanesulfonyl)imide, bis(perfluoroethanesulfonyl) imide, bis(perfluorobutanesulfonyl)imide, tris(trifluoromethanesulfonyl)methide, and tris(perfluoroethanesulfonyl)methide. Sulfonium salts based on combination of the foregoing examples are included.

Iodinium salts are salts of iodonium cations with sulfonates. Exemplary iodinium cations are aryliodonium cations including diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4'-toluenesulfonyloxy)benzenesulfonate, 6-(4-toluenesulfonyloxy)naphthalene-1-sulfonate, 4-(4-toluenesulfonyloxy)naphthalene-1-sulfonate, 5-(4-toluenesulfonyloxy)naphthalene-1-sulfonate, 8-(4-toluenesulfonyloxy)naphthalene-1-sulfonate, naphthalenesulfonate, camphorsulfonate, octanesulfonate, dodecylbenzenesulfonate, butanesulfonate, methanesulfonate, bis(trifluoromethanesulfonyl)imide, bis(perfluoroethanesulfonyl)imide, bis(perfluorobutanesulfonyl)imide, tris(trifluoromethanesulfonyl)methide, and tris(perfluoroethanesulfonyl)methide. Iodonium salts based on combination of the foregoing examples are included.

Exemplary sulfonyldiazomethane compounds include bissulfonyldiazomethane compounds and sulfonyl-carbonyldiazomethane compounds such as bis(ethylsulfonyl)diazomethane, bis(1-methylpropylsulfonyl)diazomethane, bis(2-methylpropylsulfonyl)diazomethane, bis(1,1-dimethylethylsulfonyl)diazomethane, bis(cyclohexylsulfonyl)diazomethane, bis(perfluoroisopropylsulfonyl)diazomethane, bis(phenylsulfonyl)diazomethane, bis(4-methylphenylsulfonyl)diazomethane, bis(2,4-dimethylphenylsulfonyl)diazomethane, bis(4-acetyloxyphenylsulfonyl)diazomethane, bis(4-methanesulfonyloxyphenylsulfonyl)diazomethane, bis(4-(4-toluenesulfonyloxy)phenylsulfonyl)diazomethane, bis(2-naphthylsulfonyl)diazomethane, 4-methylphenylsulfonylbenzoyldiazomethane, tert-butylcarbonyl-4-methylphenylsulfonyldiazomethane, 2-naphthylsulfonylbenzoyldiazomethane, 4-methylphenylsulfonyl-2-naphthoyldiazomethane, methylsulfonylbenzoyldiazomethane, and tert-butoxycarbonyl-4-methylphenylsulfonyldiazomethane.

N-sulfonyloxydicarboxyimide photoacid generators include combinations of imide skeletons with sulfonates. Exemplary imide skeletons are succinimide, naphthalenedicarboxyimide, phthalimide, cyclohexyldicarboxyimide, 5-norbornene-2,3-dicarboxyimide, and 7-oxabicyclo[2.2.1]-5-heptene-2,3-dicarboxyimide. Exemplary sulfonates include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, naphthalenesulfonate, camphorsulfonate, octanesulfonate, dodecylbenzenesulfonate, butanesulfonate, and methanesulfonate.

Benzoinsulfonate photoacid generators include benzoin tosylate, benzoin mesylate, and benzoin butanesulfonate.

Pyrogallol trisulfonate photoacid generators include pyrogallol, fluoroglycine, catechol, resorcinol, hydroquinone, in which all the hydroxyl groups are substituted with trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate or the like.

Nitrobenzyl sulfonate photoacid generators include 2,4-dinitrobenzyl sulfonate, 2-nitrobenzyl sulfonate, and 2,6-dinitrobenzyl sulfonate, with exemplary sulfonates including trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, and methanesulfonate. Also useful are analogous nitrobenzyl sulfonate compounds in which the nitro group on the benzyl side is substituted with a trifluoromethyl group.

Sulfone photoacid generators include bis(phenylsulfonyl)methane, bis(4-methylphenylsulfonyl)methane, bis(2-naphthylsulfonyl)methane, 2,2-bis(phenylsulfonyl)propane, 2,2-bis(4-methylphenylsulfonyl)propane, 2,2-bis(2-naphthylsulfonyl)propane, 2-methyl-2-(p-toluenesulfonyl)propiophenone, 2-cyclohexylcarbonyl-2-(p-toluenesulfonyl)propane, and 2,4-dimethyl-2-(p-toluenesulfonyl)pentan-3-one.

Suitable O-arylsulfonyloxime compounds and O-alkylsulfonyloxime compounds (oxime sulfonates) include photoacid generators in the form of glyoxime derivatives (Japanese Patent No. 2906999 and JP-A 9-301948), oxime sulfonates having long conjugated systems separated by thiphene or cyclohexadiene (U.S. Pat. No. 6,004,724), oxime sulfonates having an electron attractive group such as trifluoromethyl incorporated for enhanced stability (U.S. Pat. No. 6,261,738 and JP-A 2000-314956), oxime sulfonates based on phenyl acetonitrile or substituted acetonitrile derivatives (JP-A 9-95479, JP-A 9-230588 and the references cited therein), and bisoxime sulfonates (JP-A 9-208554, GB 2,348,644A, JP-A 2002-278053).

When the photoacid generator (C) is added to resist compositions adapted for KrF excimer laser lithography, use is preferably made of sulfonium salts, bissulfonyldiazomethanes, N-sulfonyloxydicarboxyimides and oxime sulfonates. Illustrative examples include triphenylsulfonium p-toluenesulfonate, triphenylsulfonium camphorsulfonate, triphenylsulfonium pentafluorobenzenesulfonate, triphenylsulfonium nonafluorobutanesulfonate, triphenylsulfonium 4-(4'-toluenesulfonyloxy)benzenesulfonate, triphenylsulfonium 2,4,6-triisopropylbenzenesulfonate, 4-tert-butoxyphenyldiphenylsulfonium p-toluenesulfonate, 4-tert-butoxyphenyldiphenylsulfonium camphorsulfonate, 4-tert-butoxyphenyldiphenylsulfonium 4-(4'-toluene-sulfonyloxy)benzenesulfonate, tris(4-methylphenyl)sulfonium camphorsulfonate, tris(4-tert-butylphenyl)sulfonium camphorsulfonate, bis(tert-butylsulfonyl)diazomethane, bis(cyclohexylsulfonyl)diazomethane, bis(2,4-dimethylphenylsulfonyl)diazomethane, bis(4-tert-butylphenylsulfonyl)diazomethane, N-camphorsulfonyloxy-5-norbornene-2,3-carboxylic acid imide, N-p-toluenesulfonyloxy-5-norbornene-2,3-carboxylic acid imide, 5-(10- camphorsulfonyl)oxyimino-5H-thiophen-2-ylidene, (2-methylphenyl)acetonitrile, 5-(4-toluenesulfonyl)oxyimino-5H-thiophen-2-ylidene), (2-methylphenyl)acetonitrile, etc.

When the photoacid generator (C) is added to resist compositions adapted for ArF excimer laser lithography, use is preferably made of sulfonium salts. Illustrative examples include triphenylsulfonium trifluoromethanesulfonate, triphenylsulfonium pentafluorobenzenesulfonate, triphenylsulfonium nonafluorobutanesulfonate, diphenyl-4-methylphenylsulfonium nonafluorobutanesulfonate, 2-oxo-2-phenylethylthiacyclopentanium nonafluorobutanesulfonate, etc.

An appropriate amount of the second photoacid generator (C) added to the chemically amplified resist composition is 0 to 10 parts, and especially 0 to 5 parts by weight per 100 parts by weight of the solids in the composition though it is not limited thereto as long as the benefits of the invention are not compromised. Too high a proportion of the second photoacid generator (C) may give rise to problems of degraded resolution and foreign matter upon development and resist film peeling. The second photoacid generators may be used alone or in admixture of two or more. The transmittance of the resist film can be controlled by using a (second) photoacid generator having a low transmittance at the exposure wavelength and adjusting the amount of the photoacid generator added.

In the resist composition of the invention, there may be added a compound which is decomposed with an acid to generate another acid, that is, acid-propagating compound. For these compounds, reference should be made to J. Photopolym. Sci. and Tech., 8, 43–44, 45–46 (1995), and ibid., 9, 29–30 (1996).

Examples of the acid-propagating compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid-propagating compound-like behavior.

In the resist composition of the invention, an appropriate amount of the acid-propagating compound is up to 2 parts, and especially up to 1 part by weight per 100 parts by weight of the solids in the composition. Excessive amounts of the acid-propagating compound makes diffusion control difficult, leading to degradation of resolution and pattern configuration.

Component (D)

The basic compound used as component (D) is preferably a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure and reduces substrate and environment dependence, as well as improving the exposure latitude and the pattern profile.

Examples of basic compounds include primary, secondary, and tertiary aliphatic amines, mixed amines, aromatic amines, heterocyclic amines, carboxy group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Illustrative examples of the basic compounds are described in JP-A 11-84639, JP-A 2002-226470, JP-A 2002-249478, JP-A 2002-363146, JP-A 2002-363148, JP-A 2002-363152, and JP-A 2001-122850.

The basic compounds may be used alone or in admixture of two or more. The basic compound is preferably formulated in an amount of 0 to 2 parts, and especially 0.01 to 1 part by weight, per 100 parts by weight of the solids in the resist composition. The use of more than 2 parts of the basis compound would result in too low a sensitivity.

Component (E)

Illustrative, non-limiting, examples of the organic acid derivatives (E) include phenol, cresol, catechol, resorcinol, pyrogallol, fluoroglycin, bis(4-hydroxyphenyl)methane, 2,2-bis(4'-hydroxyphenyl)propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl)valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more.

In the resist composition of the invention, the organic acid derivative is preferably formulated in an amount of up to 5 parts, and especially up to 1 part by weight, per 100 parts by weight of the solids in the resist composition. The use of more than 5 parts of the organic acid derivative would result in too low a resolution. Depending on the combination of the other components in the resist composition, the organic acid derivative may be omitted.

Component (F)

Component (F) is an organic solvent. Illustrative, non-limiting, examples include butyl acetate, amyl acetate, cyclohexyl acetate, 3-methoxybutyl acetate, methyl ethyl ketone, methyl amyl ketone, cyclohexanone, cyclopentanone, 3-ethoxyethyl propionate, 3-ethoxymethyl propionate, 3-methoxymethyl propionate, methyl acetoacetate, ethyl acetoacetate, diacetone alcohol, methylpyruvate, ethyl pyruvate, propylene glycol monomethyl ether, propylene glycol monoethyl ether, propylene glycol monomethyl ether propionate, propylene glycol monoethyl ether propionate, ethylene glycol monomethyl ether, ethylene glycol monoethyl ether, diethylene glycol monomethyl ether, diethylene glycol monoethyl ether, 3-methyl-3-methoxybutanol, N-methylpyrrolidone, dimethyl sulfoxide, γ-butyrolactone, propylene glycol methyl ether acetate, propylene glycol ethyl ether acetate, propylene glycol propyl ether acetate, methyl lactate, ethyl lactate, propyl lactate, and tetramethyl sulfone. Of these, the propylene glycol alkyl ether acetates and alkyl lactates are especially preferred. The solvents may be used alone or in admixture of two or more. An exemplary useful solvent mixture is a mixture of a propylene glycol alkyl ether acetate and an alkyl lactate. It is noted that the alkyl groups of the propylene glycol alkyl ether acetates are preferably those of 1 to 4 carbon atoms, for example, methyl, ethyl and propyl, with methyl and ethyl being especially preferred. Since the propylene glycol alkyl ether acetates include 1,2- and 1,3-substituted ones, each includes three isomers depending on the combination of substituted positions, which may be used alone or in admixture. It is also noted that the alkyl groups of the alkyl lactates are preferably those of 1 to 4 carbon atoms, for example, methyl, ethyl and propyl, with methyl and ethyl being especially preferred.

The solvent is preferably used in an amount of 300 to 2,000 parts by weight, especially 400 to 1,000 parts by weight per 100 parts by weight of the solids in the resist composition. The solvent concentration is not limited thereto as long as a film can be formed by existing methods.

Component (G)

In one preferred embodiment, the resist composition further contains (G) a compound with a molecular weight of up to 3,000 which changes its solubility in an alkaline developer under the action of an acid, that is, a dissolution inhibitor. Typically, a compound obtained by partially or entirely substituting acid labile substituents on a phenol or carboxylic acid derivative having a molecular weight of up to 2,500 is added as the dissolution inhibitor.

Examples of the phenol or carboxylic acid derivative having a molecular weight of up to 2,500 include bisphenol A, bisphenol H, bisphenol S, 4,4-bis(4'-hydroxyphenyl) valeric acid, tris(4-hydroxyphenyl)methane, 1,1,1-tris(4'-hydroxyphenyl)ethane, 1,1,2-tris(4'-hydroxyphenyl)ethane, phenolphthalein, thymolphthalein, cholic acid, deoxycholic acid, and lithocholic acid. The acid labile substituents are the same as those exemplified as the acid labile groups in the polymer.

Illustrative, non-limiting, examples of the dissolution inhibitors which are useful herein include bis(4-(2'-tetrahydropyranyloxy)phenyl)methane, bis(4-(2'-tetrahydrofuranyloxy)phenyl)methane, bis(4-tert-butoxyphenyl)methane, bis(4-tert-butoxycarbonyloxyphenyl)methane, bis(4-tert-butoxycarbonylmethyloxyphenyl)methane, bis(4-(1'-ethoxyethoxy)phenyl)methane, bis(4-(1'-ethoxypropyloxy) phenyl)methane, 2,2-bis(4'-(2"-tetrahydropyranyloxy)) propane, 2,2-bis(4'-(2"-tetrahydrofuranyloxy)phenyl) propane, 2,2-bis(4'-tert-butoxyphenyl)propane, 2,2-bis(4'-tert-butoxycarbonyloxyphenyl)propane, 2,2-bis(4-tert-butoxycarbonylmethyloxyphenyl)propane, 2,2-bis(4'-(1"-ethoxyethoxy)phenyl)propane, 2,2-bis(4'-(1"-ethoxypropyloxy)phenyl)propane, tert-butyl 4,4-bis(4'-(2"-tetrahydropyranyloxy)phenyl)-valerate, tert-butyl 4,4-bis (4'-(2"-tetrahydrofuranyloxy)phenyl)-valerate, tert-butyl 4,4-bis(4'-tert-butoxyphenyl)valerate, tert-butyl 4,4-bis(4-tert-butoxycarbonyloxyphenyl)valerate, tert-butyl 4,4-bis (4'-tert-butoxycarbonylmethyloxyphenyl)-valerate, tert-butyl 4,4-bis(4'-(1"-ethoxyethoxy)phenyl)valerate, tert-butyl 4,4-bis(4'-(1"-ethoxypropyloxy)phenyl)valerate, tris(4-(2'-tetrahydropyranyloxy)phenyl)methane, tris(4-(2'-tetrahydrofuranyloxy)phenyl)methane, tris(4-tert-butoxyphenyl) methane, tris(4-tert-butoxycarbonyloxyphenyl)methane, tris (4-tert-butoxycarbonyloxymethylphenyl)methane, tris(4-(1'-ethoxyethoxy)phenyl)methane, tris(4-(1'-ethoxypropyloxy)phenyl)methane, 1,1,2-tris(4'-(2"-tetrahydropyranyloxy)phenyl)ethane, 1,1,2-tris(4'-(2"-tetrahydrofuranyloxy)phenyl)ethane, 1,1,2-tris(4'-tert-butoxyphenyl)ethane, 1,1,2-tris(4'-tert-butoxycarbonyloxyphenyl)ethane, 1,1,2-tris(4'-tert-butoxycarbonylmethyloxyphenyl)ethane, 1,1,2-tris(4'-(1'-ethoxyethoxy)phenyl)ethane, 1.1, 2-tris(4'-(1'-ethoxypropyloxy)phenyl)ethane, t-butyl cholate, t-butyl deoxycholate, and t-butyl lithocholate.

In the resist composition of the invention, an appropriate amount of the dissolution inhibitor (G) is up to 20 parts, and especially up to 15 parts by weight per 100 parts by weight of the solids in the resist composition. With more than 20 parts of the dissolution inhibitor, the resist composition becomes less heat resistant because of an increased content of monomer components.

Component (H)

The photoacid generator of the invention is also applicable to a chemical amplification, negative working, resist composition. This composition further contains an alkali-soluble resin as component (H). The resins used herein may be the aforementioned base resins prior to substitution with acid labile groups. Examples of the alkali-soluble resin include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxystyrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, but are not limited to these combinations.

To impart a certain function, suitable substituent groups may be introduced into some of the phenolic hydroxyl and carboxyl groups on the foregoing polymer. Exemplary and preferred are substituent groups for improving adhesion to the substrate, substituent groups for improving etching resistance, and especially substituent groups which are relatively stable to acid and alkali and effective for controlling such that the dissolution rate in an alkali developer of unexposed and low exposed areas of a resist film may not become too high. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, n-propyl, isopropyl, n-butyl, sec-butyl, acetyl, pivaloyl, adamantyl, isoboronyl, and cyclohexyl. It is also possible to introduce acid-decomposable substituent groups such as t-butoxycarbonyl and relatively acid-undecomposable substituent groups such as t-butyl and t-butoxycarbonylmethyl.

In the resist composition, the above resin is blended in any desired amount, preferably of 65 to 99 parts by weight, especially 65 to 98 parts by weight per 100 parts by weight of the solids.

Also contained in the negative resist composition is (I) an acid crosslinking agent capable of forming a crosslinked structure under the action of an acid. Typical acid crosslinking agents are compounds having at least two hydroxymethyl, alkoxymethyl, epoxy or vinyl ether groups in a molecule. Substituted glycoluril derivatives, urea derivatives, and hexa(methoxymethyl)melamine compounds are suitable as the acid crosslinking agent in the chemically amplified, negative resist composition of the invention. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis(hydroxymethylphenol) compounds and bisphenol A with epichlorohydrin. Especially preferred acid crosslinking agents are 1,3,5,7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N',N'-tetramethoxymethylurea, and hexamethoxymethylmelamine.

An appropriate amount of the acid crosslinking agent is, but not limited thereto, about 1 to 20 parts, and especially about 5 to 15 parts by weight per 100 parts by weight of the solids in the resist composition. The acid crosslinking agents may be used alone or in admixture of any.

In the chemical amplification type resist composition of the invention, there may be added such additives as a surfactant for improving coating, and a light absorbing agent for reducing diffuse reflection from the substrate.

Illustrative, non-limiting, examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (Tohkem Products Co., Ltd.), Megaface F171, F172 and F173 (Dai-Nippon Ink & Chemicals, Inc.), Fluorad FC430 and FC431 (Sumitomo 3M Co., Ltd.), Aashiguard AG710, Surflon S-381, S-382, SC101, SC102, SC103, SC104, SC105, SC106, Surfynol E1004, KH-10, KH-20, KH-30 and KH-40 (Asahi Glass Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo Co., Ltd.). Inter alia, FC430, Surflon S-381, Surfynol E1004, KH-20 and KH-30 are preferred. These surfactants may be used alone or in admixture.

In the chemically amplified resist composition according to the invention, the surfactant is preferably formulated in an amount of up to 2 parts, and especially up to 1 part by weight, per 100 parts by weight of the solids in the resist composition.

In the chemically amplified resist composition according to the invention, a UV absorber may be added. Those UV absorbers described in JP-A 11-190904 are useful, but the invention is not limited thereto. Exemplary UV absorbers are diaryl sulfoxide derivatives such as bis(4-hydroxyphenyl)sulfoxide, bis(4-tert-butoxyphenyl)sulfoxide, bis(4-tert-butoxycarbonyloxyphenyl)sulfoxide, and bis[4-(1-ethoxyethoxy)phenyl]sulfoxide; diarylsulfone derivatives such as bis(4-hydroxyphenyl)sulfone, bis(4-tert-butoxyphenyl)sulfone, bis(4-tert-butoxycarbonyloxyphenyl)sulfone, bis[4-(1-ethoxyethoxy)phenyl]sulfone, and bis[4-(1-ethoxypropoxy)phenyl]sulfone; diazo compounds such as benzoquinonediazide, naphthoquinonediazide, anthraquinonediazide, diazofluorene, diazotetralone, and diazophenanthrone; quinonediazide group-containing compounds such as complete or partial ester compounds between naphthoquinone-1,2-diazide-5-sulfonic acid chloride and 2,3,4-trihydroxybenzophenone and complete or partial ester compounds between naphthoquinone-1,2-diazide-4-sulfonic acid chloride and 2,4,4'-trihydroxybenzophenone; tert-butyl 9-anthracenecarboxylate, tert-amyl 9-anthracenecarboxylate, tert-methoxymethyl 9-anthracenecarboxylate, tert-ethoxyethyl 9-anthracenecarboxylate, 2-tert-tetrahydropyranyl 9-anthracenecarboxylate, and 2-tert-tetrahydrofuranyl 9-anthracenecarboxylate. The UV absorber may or may not be added to the resist composition depending on the type of resist composition. An appropriate amount of UV absorber, if added, is 0 to 10 parts, more preferably 0.5 to 10 parts, most preferably 1 to 5 parts by weight per 100 parts by weight of the base resin.

Pattern formation using the resist composition of the invention may be carried out by a known lithographic technique. For example, the resist composition is applied onto a substrate such as a silicon wafer by spin coating or the like to form a resist film having a thickness of 0.1 to 2.0 μm, which is then pre-baked on a hot plate at 60 to 150° C. for 1 to 10 minutes, and preferably at 80 to 130° C. for 1 to 5 minutes. A patterning mask having the desired pattern is then placed over the resist film, and the film exposed through the mask to an ArF excimer laser beam in a dose of about 1 to 100 mJ/cm$^2$, and preferably about 5 to 50 mJ/cm$^2$, then post-exposure baked (PEB) on a hot plate at 60 to 150° C. for 1 to 5 minutes, and preferably at 80 to 130° C. for 1 to 3 minutes. Finally, development is carried out using as the developer an aqueous alkali solution, such as a 0.1 to 5% (preferably 2 to 3%) aqueous solution of tetramethylammonium hydroxide (TMAH), this being done by a conventional method such as dipping, puddling, or spraying for a period of 0.1 to 3 minutes, and preferably 0.5 to 2 minutes. These steps result in the formation of the desired pattern on the substrate. The desired pattern may not be obtainable outside the upper and lower limits of the above range.

The resist composition comprising the photoacid generator according to the invention has many advantages including excellent resolution, thermal stability, storage stability, and minimized line edge roughness.

EXAMPLE

Examples of the invention are given below by way of illustration and not by way of limitation.

Synthesis Example 1

Synthesis of 2-methoxy-1-naphthyltetrahydrothiophenium perfluorobutanesulfonate

Tetramethylene sulfoxide, 2.9 g (0.05 mol), was added to 7.9 g (0.05 mol) of 2-methoxynaphthalene and 15 g of Eaton's reagent (Aldrich), followed by 24 hours of stirring at room temperature. 200 g of water and 100 g of diethyl ether were added to the reaction mixture for separation into two layers. To the aqueous layer, 8.5 g (0.025 mol) of potassium perfluorobutanesulfonate and 100 g of dichloromethane were added, followed by one hour of stirring at room temperature. The organic layer separated was washed three times with 50 g of water, after which the solvent was evaporated off on a rotary evaporator. The oily matter was recrystallized from diethyl ether, filtered and dried. There was obtained 10.4 g of the end compound, 2-methoxy-1-naphthyltetrahydrothiophenium perfluorobutanesulfonate (yield: 76% based on the potassium perfluorobutanesulfonate).

The sulfonium salt thus obtained was analyzed by nuclear magnetic resonance (NMR) spectroscopy, infrared (IR) absorption spectroscopy, and time-of-flight mass spectroscopy (TOF-MS), with the results shown below.

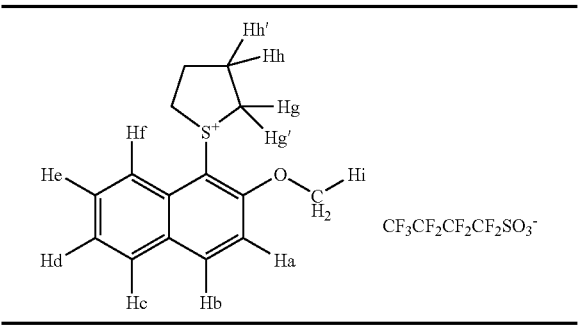

$^1$H-NMR(CDCl$_3$): ppm

| | | | |
|---|---|---|---|
| 1) Ha, Hd or He | 7.440–7.470 | 2H | multiplet |
| 2) Hb | 8.197–8.227 | 1H | doublet |
| 3) Hc or Hf | 7.845–7.864 | 1H | doublet |
| 4) He or Hd | 7.647–7.713 | 1H | triplet |
| 5) Hf or Hc | 8.384–8.415 | 1H | doublet |
| 6) Hg, Hg' | 3.737–4.033 | 2H | multiplet |
| 7) Hh, Hh' | 2.435–2.785 | 2H | multiplet |
| 8) Hi | 4.187 | 3H | singlet |

IR: cm$^{-1}$ 2972, 1626, 1595, 1512, 1464, 1433, 1354, 1338, 1265, 1209, 1157, 1132, 1057, 1020, 980, 831, 802, 771, 748, 735, 656, 638, 617, 600, 534, 523

MALDI-TOFMS (+) 245
(−) 299

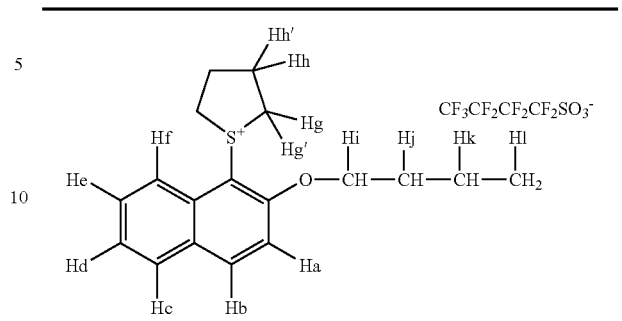

$^1$H-NMR(CDCl$_3$): ppm

| | | | |
|---|---|---|---|
| 1) Ha, Hd or He | 7.430–7.505 | 2H | multiplet |
| 2) Hb | 8.184–8.215 | 1H | doublet |
| 3) Hc or Hf | 7.833–7.862 | 1H | doublet |
| 4) He or Hd | 7.659–7.715 | 1H | triplet |
| 5) Hf or Hc | 8.436–8.467 | 1H | doublet |
| 6) Hg, Hg' | 3.788–4.087 | 2H | multiplet |
| 7) Hh, Hh' | 2.500–2.762 | 2H | multiplet |
| 8) Hi | 4.400–4.470 | 2H | triplet |
| 9) Hj | 1.877–1.975 | 2H | multiplet |
| 10) Hk | 1.426–1.550 | 2H | multiplet |
| 11) Hl | 0.990–1.039 | 3H | triplet |

IR: cm$^{-1}$ 1624, 1597, 1512, 1475, 1464, 1435, 1352, 1338, 1267, 1234. 1211, 1190, 1155, 1132, 1055, 1018, 1007, 984, 957, 870, 808, 771, 750, 735, 698, 654, 638, 617, 600, 565, 532

MALDI-TOFMS (+) 287
(−) 299

Synthesis Example 2

Synthesis of 2-n-butoxy-1-naphthyltetrahydrothiophenium perfluorobutanesulfonate In 100 g of ethanol were dissolved 50 g (0.347 mol) of 2-naphthol and 14.6 g (0.364 mol) of sodium hydroxide. Under reflux, 50 g (0.364 mol) of n-butyl bromide was added to the solution, which was refluxed for a further 4 hours. To the reaction solution were added 200 g of water and 4 g of sodium hydroxide. The organic layer thus separated, 75 g, was distilled in vacuo, obtaining 59 g of 2-n-butoxynaphthalene. The distillate (liquid) solidified when allowed to stand at room temperature.

Next, 2.9 g (0.05 mol) of tetramethylene sulfoxide was added to 5.0 g (0.025 mol) of the 2-n-butoxynaphthalene and 15 g of Eaton's reagent (Aldrich), followed by 24 hours of stirring at room temperature. 200 g of water and 50 g of diethyl ether were added to the reaction mixture for separation into two layers. To the aqueous layer, 8.5 g (0.025 mol) of potassium perfluorobutanesulfonate and 100 g of dichloromethane were added, followed by one hour of stirring at room temperature. The organic layer separated was washed three times with 50 g of water, after which the solvent was evaporated off on a rotary evaporator. The oily matter was recrystallized from ethyl acetate, filtered and dried. There was obtained 13.8 g of the end compound, 2-n-butoxy-1-naphthyltetrahydrothiophenium perfluorobutanesulfonate (yield 94%).

The sulfonium salt thus obtained was analyzed by NMR, IR, and TOF-MS, with the results shown below.

Synthesis Example 3

Synthesis of 2-methoxy-1-naphthyldimethylsulfonium perfluorobutanesulfonate

The end compound was synthesized as in Synthesis Example 1 aside from using dimethyl sulfoxide instead of tetramethylene sulfoxide in Synthesis Example 1.

Synthesis Example 4

Synthesis of 2-n-butoxy-1-naphthyldimethylsulfonium perfluorobutanesulfonate

The end compound was synthesized as in Synthesis Example 2 aside from using dimethyl sulfoxide instead of tetramethylene sulfoxide in Synthesis Example 2.

Synthesis Example 5

Synthesis of 2-n-butoxy-1-naphthyltetrahydrothiephenium trifluoromethanesulfonate The end compound was synthesized as in Synthesis Example 2 aside from using sodium trifluoromethanesulfonate instead of potassium perfluorobutanesulfonate in Synthesis Example 2.

Synthesis Example 6

Synthesis of 2-cyclohexyloxy-1-naphthyltetrahydrothiophenium perfluorobutanesulfonate The end compound was synthesized as in Synthesis Example 1 aside from using 2-cyclohexyloxynaphthalene instead of 2-methoxynaphthalene in Synthesis Example 1.

Evaluating Example

The photoacid generators PAG1 to PAG10 shown below, when formulated into resist compositions, were examined for sensitivity and resolution.

(PAG1)
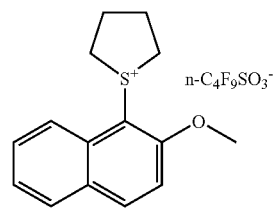

(PAG2)
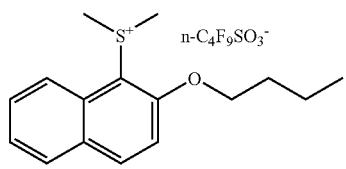

(PAG3)
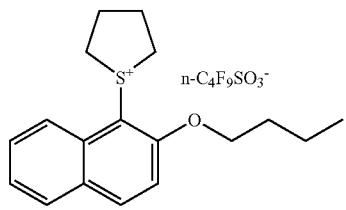

(PAG4)
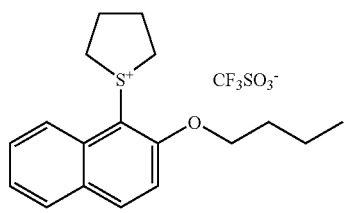

(PAG5)
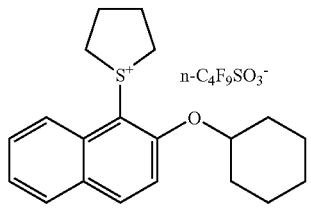

(PAG6)
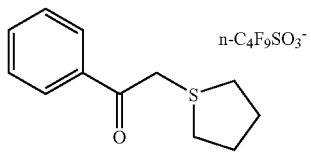

(PAG7)
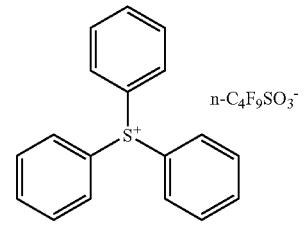

(PAG8)
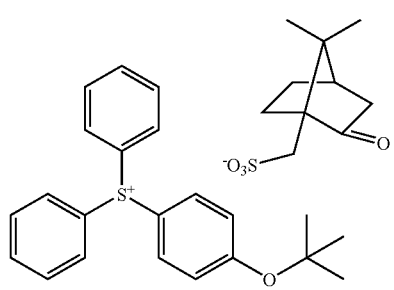

(PAG9)
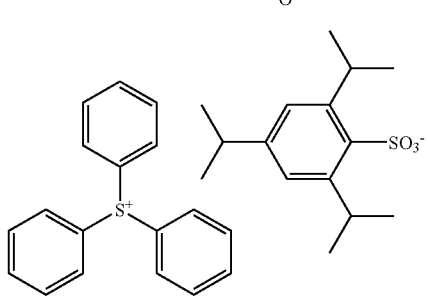

(PAG10)
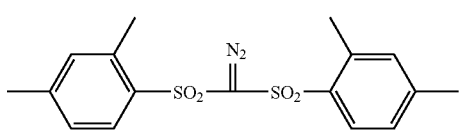

Examples 1–41

Resolution of Resist

Resist compositions were prepared by using PAG1 to PAG10 as the photoacid generator and Polymers 1 to 28 as the base resin, and dissolving the polymer and photoacid generator in a solvent along with a dissolution inhibitor (DRR1 to 4), a basic compound and an organic acid derivative (ACC1 and 2). The solvent contained 0.01 wt % of FC-430 (3M-Sumitomo Co., Ltd.). The resist compositions were each filtered through a 0.2-μm Teflon® filter, thereby giving resist solutions.
(Polymer 1)
(b1 = 0.40, d1 = 0.60, Mw = 11,200)
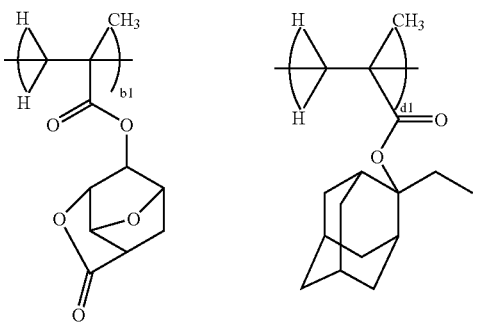
(Polymer 2)
(b1 = 0.50, d1 = 0.50, Mw = 11,800)
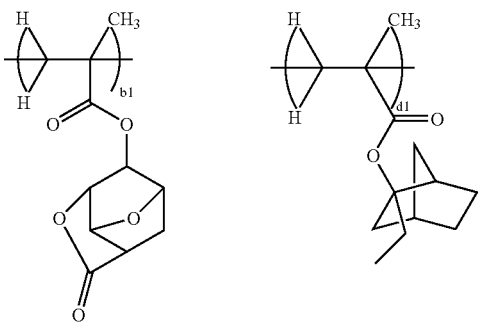
(Polymer 3)
(b1 = 0.50, d1 = 0.50, Mw = 10,900)
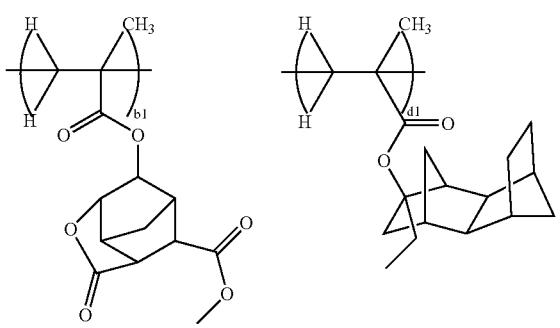
(Polymer 4)
(d1 = 0.30, d2 = 0.35, e = 0.35, Mw = 10,500)
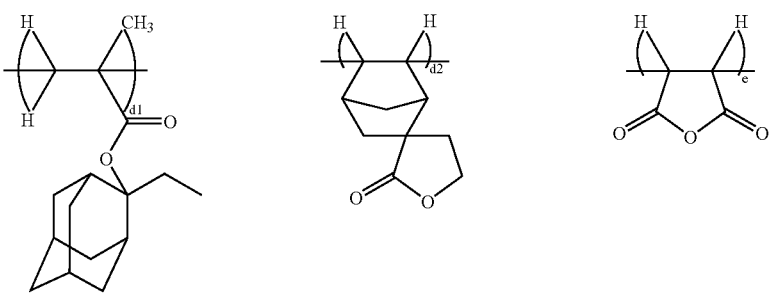

-continued
(Polymer 5)
(b1 = 0.40, d1 = 0.30, d2 = 0.30, Mw = 12,500)
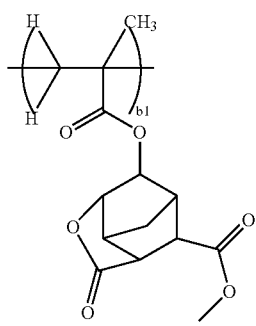 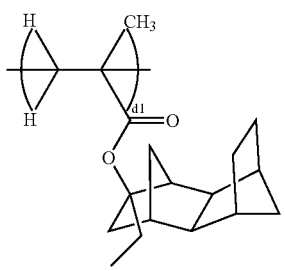 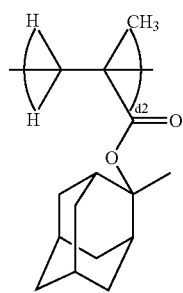
(Polymer 6)
(b1 = 0.40, b2 = 0.30, d1 = 0.30, Mw = 11,200)
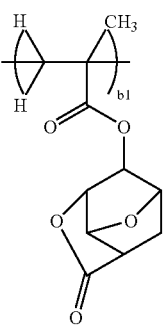 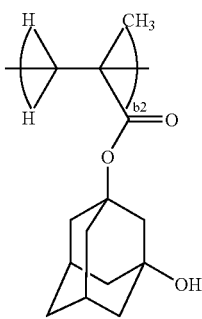 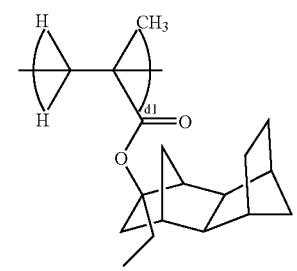
(Polymer 7)
(b1 = 0.40, b2 = 0.20, d1 = 0.40, Mw = 12,800)
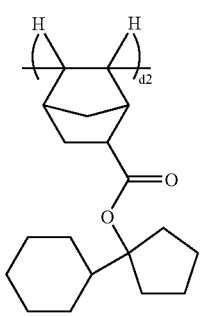 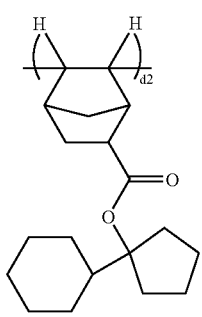 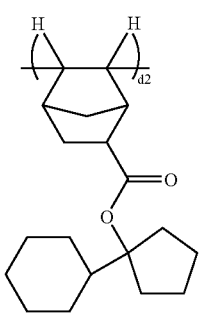
(Polymer 8)
(d2 = 0.35, b2 = 0.15, e = 0.50, Mw = 8,300)
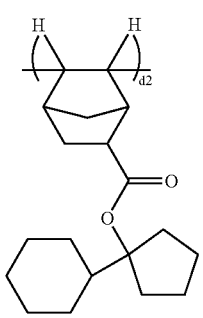 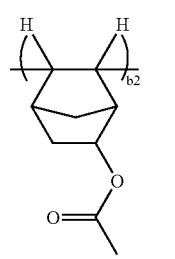 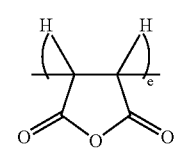
(Polymer 9)
(a2 = 0.10, b2 = 0.30, d1 = 0.60, Mw = 27,600)
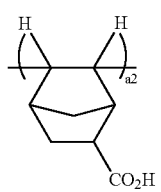 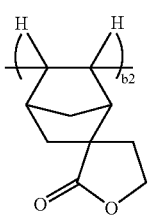 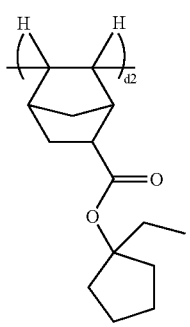

(Polymer 10)
(b2 = 0.40, d2 = 0.60, Mw = 18,300)
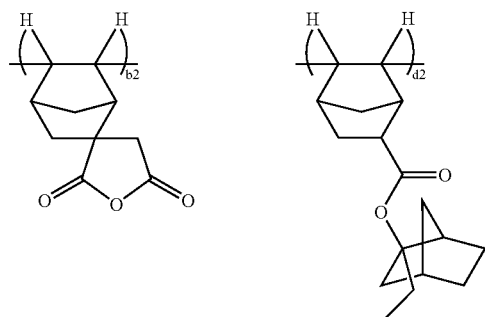
(Polymer 11)
(b3 = 0.50, d3 = 0.50, Mw = 29,100)
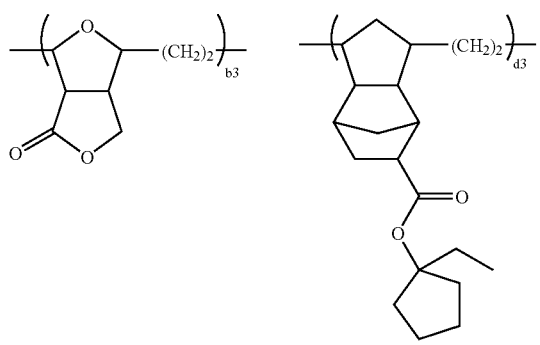
(Polymer 12)
(d2 = 0.50, e = 0.50, Mw = 8,300)
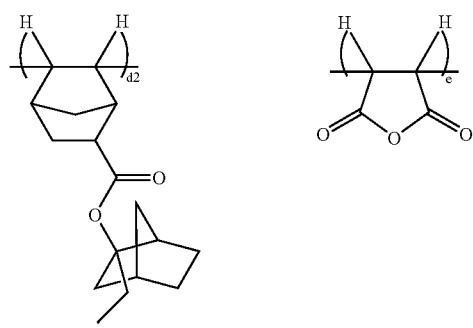
(Polymer 13)
(a2 = 0.10, b2 = 0.30, d1 = 0.60, Mw = 27,600)
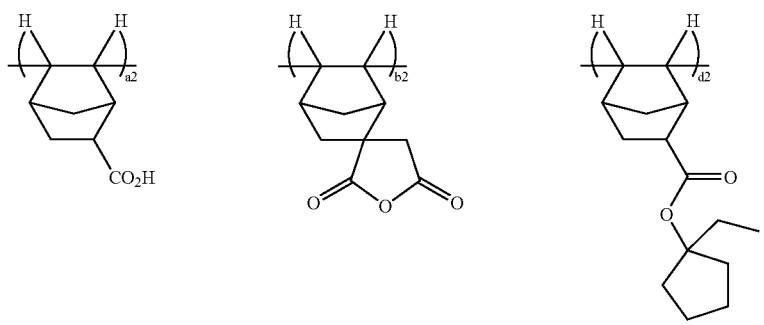

-continued
(Polymer 14)
(b2 = 0.40, d2 = 0.60, Mw = 18,300)
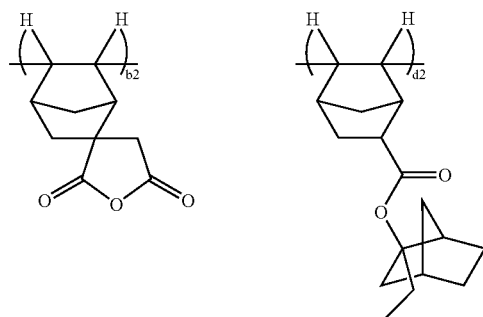
(Polymer 15)
(b3 = 0.40, d3 = 0.60, Mw = 29,100)
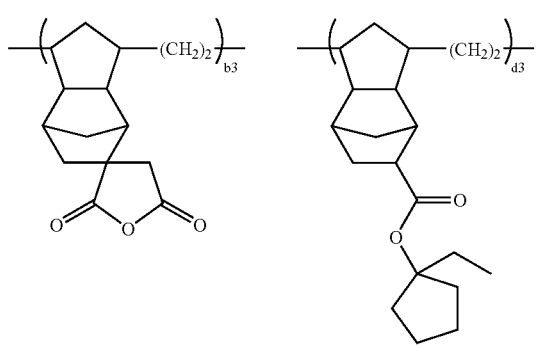
(Polymer 16)
(d1 = 0.40, S = 0.20,
e = 0.40, Mw = 10,200)
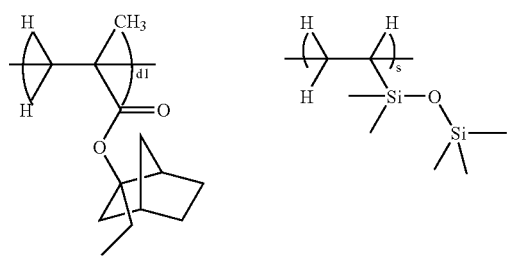
(Polymer 17)
(d1 = 0.45, S = 0.10,
e = 0.45, Mw = 12,200)
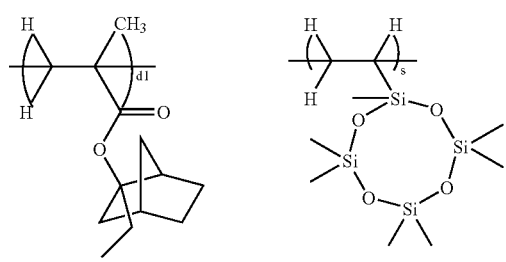
(Polymer 18)
(d1 = 0.45, S = 0.10,
e = 0.45, Mw = 14,200)
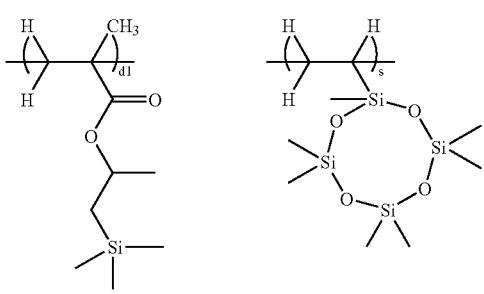

-continued
(Polymer 19)
(d1 = 0.45, S = 0.10,
e = 0.45, Mw = 10,200)
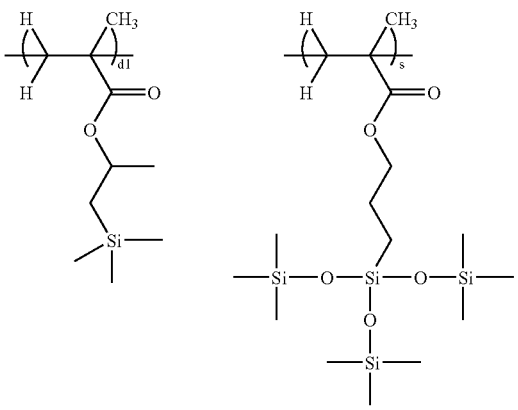
(Polymer 20)
(d1 = 0.45, S = 0.10,
e = 0.45, Mw = 12,600)
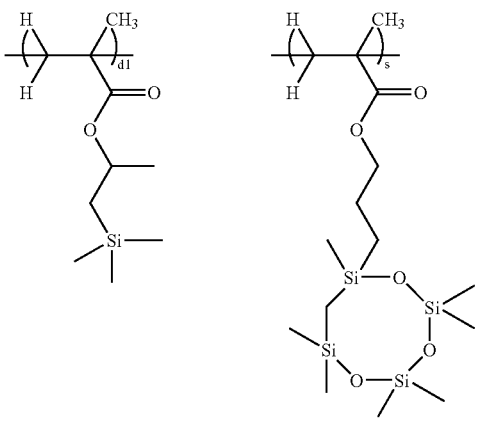
(Polymer 21)
(f1 = 0.70, d1 = 0.30, Mw = 14,200)
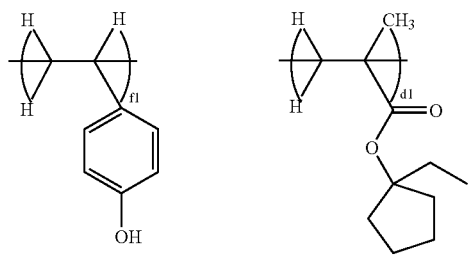
(Polymer 22)
(f1 = 0.65, d1 = 0.35, Mw = 13,600)
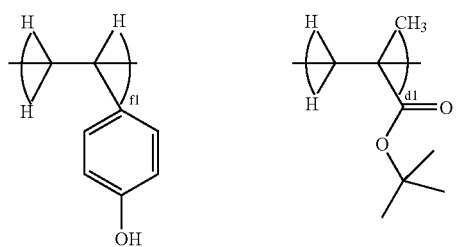
(Polymer 23)
(f1 = 0.65, g2 = 0.20, d1 = 0.15,
Mw = 12,200)
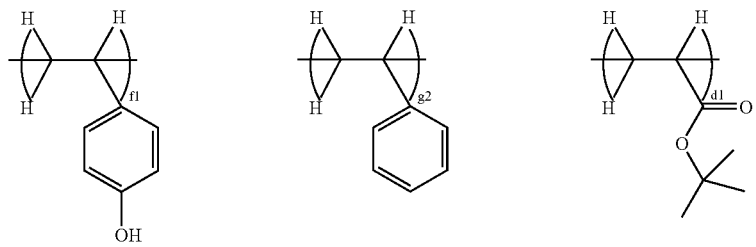

-continued
(Polymer 24)
(f1 = 0.70, g1 = 0.15, d1 = 0.15, Mw = 8,900)
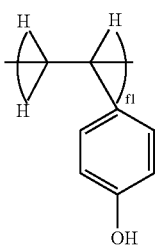 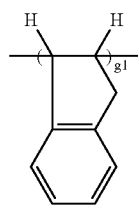 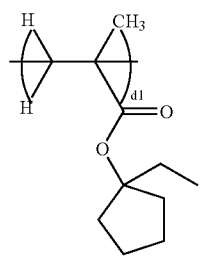
(Polymer 25)
(f1 = 0.75, g1 = 0.13, d1 = 0.12, Mw = 9,800)
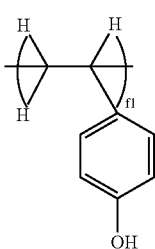 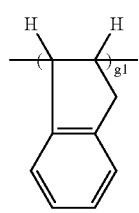 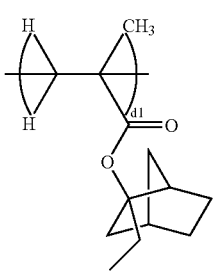
(Polymer 26)
(f1 = 0.85, d1 = 0.15, Mw = 10,900)
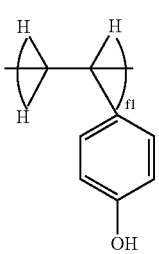 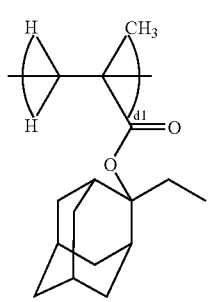
(Polymer 27)
(f1 = 0.65, f2 = 0.35, Mw = 11,000)
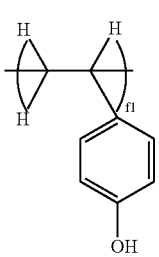 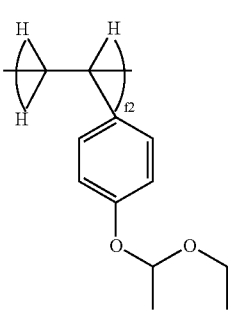
(Polymer 28)
(f1 = 0.65, f2 = 0.20, f3 = 0.15, Mw = 11,000)
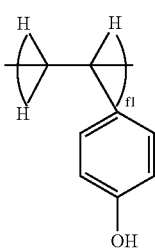 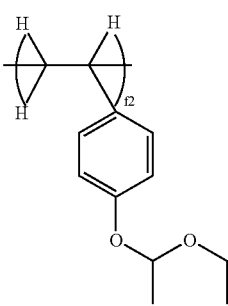 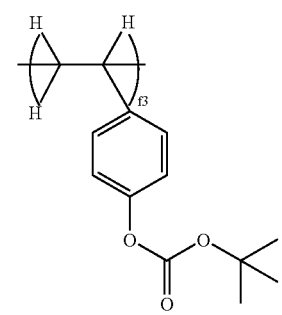

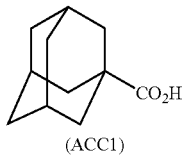
(ACC1)

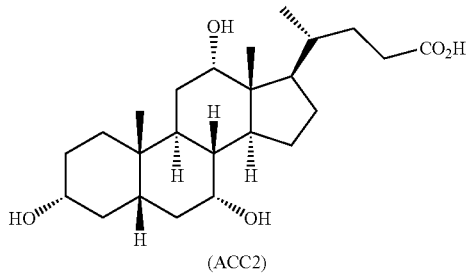
(ACC2)

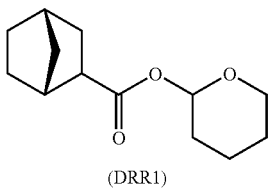
(DRR1)

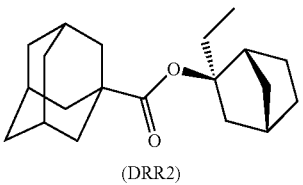
(DRR2)

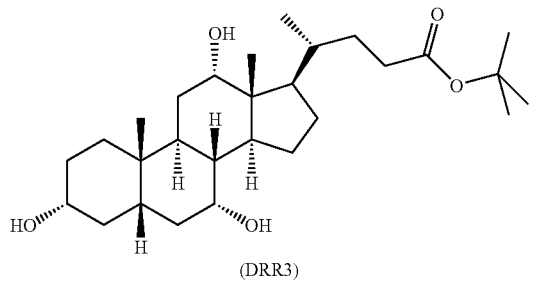
(DRR3)

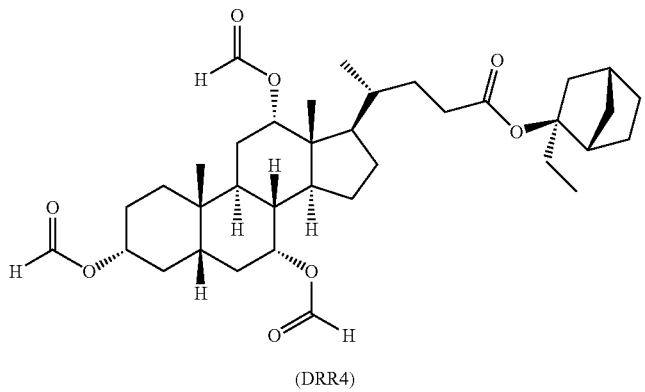
(DRR4)

ArF Exposure

The resist compositions using Polymers 1 to 20 were subjected to ArF exposure (wavelength 193 nm).

An antireflection film-forming solution (AR19 by Shipley Co.) was coated on a silicon substrate and baked at 200° C. for 60 seconds to form an antireflection film of 82 nm thick. The resin solution was spin coated on the antireflection film-coated substrate and baked on a hot plate at 110° C. for 60 seconds to form a resist film of 300 nm thick. The resist film was exposed on an ArF excimer laser micro-stepper (Nikon Corp., NA=0.55, σ=0.7), then baked (PEB) at 110° C. for 90 seconds, and developed with a 2.38% aqueous solution of tetramethylammonium hydroxide for 30 seconds.

The optimum exposure (Eop, $mJ/cm^2$) was defined as the exposure dose which provided a 1:1 resolution to a line-and-space pattern of 0.20 µm group. The resolution of the resist under evaluation was defined as the minimum line width (µm) of the lines and spaces that separated at the optimum exposure. The width of an isolated line in a 1:10 line-and-space pattern at the same exposure was measured, and the width of an isolated line subtracted from the width of the grouped lines was the size difference between isolated and densely packed patterns (I/G bias). The group lines were examined for roughness, which was reported as line edge roughness.

Storage stability was judged in terms of foreign matter precipitation or sensitivity change with the passage of time. After the resist solution was aged for 100 days at the longest, the number of particles of greater than 0.3 µm per ml of the resist solution was counted by means of a particle counter KL-20A (Rion Co., Ltd.), and the foreign matter precipitation was determined "good" when the number of particles is not more than 5. Also, the sensitivity change was rated "good" when a change with time of sensitivity (Eop) was within 5% from that immediately after preparation, and "poor" when the change is more than 5%.

The results are shown in Table 1.

KrF Exposure

The resist compositions using Polymers 21 to 28 were subjected to KrF exposure (wavelength 248 nm).

An antireflection film-forming solution (DUV-30 by Brewer Science) was coated on a silicon substrate and baked at 200° C. for 60 seconds to form an antireflection film of 55 nm thick. The resin solution was spin coated on the antireflection film-coated substrate and baked on a hot plate at 110° C. for 60 seconds to form a resist film of 400 nm thick. The resist film was exposed on a KrF excimer laser scanner S203B (Nikon Corp., NA=0.68, s=0.75), then baked (PEB) at 110° C. for 90 seconds, and developed with a 2.38% aqueous solution of tetramethylammonium hydroxide for 60 seconds.

The optimum exposure (Eop, $mJ/cm^2$) was defined as the exposure dose which provided a 1:1 resolution to a line-and-space pattern of 0.18 µm group. The resolution of the resist under evaluation was defined as the minimum line width (µm) of the lines and spaces that separated at the optimum exposure. The width of an isolated line in a 1:10 line-and-space pattern at the same exposure was measured, and the width of an isolated line subtracted from the width of the grouped lines was the size difference between isolated and densely packed patterns (I/G bias). The group lines were examined for roughness, which was reported as line edge roughness.

Storage stability was judged in terms of foreign matter precipitation or sensitivity change with the passage of time. After the resist solution was aged for 100 days at the longest, the number of particles of greater than 0.3 μm per ml of the resist solution was counted by means of a particle counter KL-20A (Rion Co., Ltd.), and the foreign matter precipitation was determined "good" when the number of particles is not more than 5. Also, the sensitivity change was rated "good" when a change with time of sensitivity (Eop) was within 5% from that immediately after preparation, and "poor" when the change is more than 5%.

The results are shown in Table 2.

The formulation of the resist compositions is shown in Tables 1 and 2 together with the test results. The solvents and basic compounds are shown below.
PGMEA: propylene glycol methyl ether acetate
CyHO: cyclohexanone
PG/EL: mixture of 70% PGMEA and 30% ethyl lactate
Each of the three solvents contained 0.01 wt % of FC-430 (3M-Sumitomo Co., Ltd.).
TBA: tributylamine
TEA: triethanol amine
TMMEA: trismethoxymethoxyethylamine
TMEMEA: trismethoxyethoxymethoxyethylamine
AAA: tris(2-acetoxyethyl)amine
AACN: N,N-bis(2-acetoxyethyl)-3-aminopropiononitrile Comparative Example For comparison purposes, the sulfonium salts (PAG6 and 7) and sulfonium salts (PAG11 to 13) shown below, when formulated into resist compositions, were examined for sensitivity and resolution.

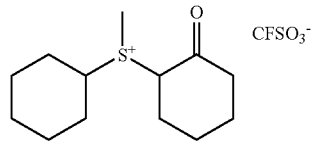
(PAG11)

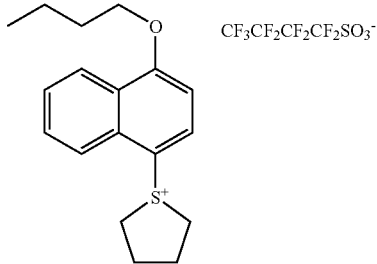
(PAG12)

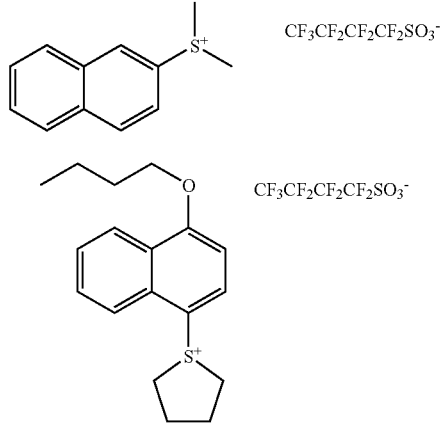
(PAG13)

Comparative Examples 1–6

As in Examples, resist compositions were prepared using the sulfonium salts (PAG6, PAG7 and PAG11 to 13) in accordance with the formulation shown in Table 3, exposed on an ArF micro-stepper, and examined for sensitivity, resolution and storage stability. The formulation of the resist compositions is shown in Table 3 together with the test results.

TABLE 1

| Example | Resin (pbw) | Photoacid generator (pbw) | Dissolution inhibitor or organic acid derivative (pbw) | Basic compound (pbw) | Solvent (pbw) | Eop (mJ/cm$^2$) | Resolution (μm) | I/G bias (nm) | Line edge roughness (nm) | Storage stability after 100 days |
|---|---|---|---|---|---|---|---|---|---|---|
| 1 | Polymer1 (80.0) | PAG1 (3.0) | — | TBA (0.1) | PGMEA (480.0) | 35 | 0.15 | 23 | 3.0 | good |
| 2 | Polymer1 (80.0) | PAG2 (3.0) | — | TBA (0.1) | PGMEA (480.0) | 38 | 0.15 | 23 | 3.0 | good |
| 3 | Polymer1 (80.0) | PAG3 (3.0) | — | TBA (0.1) | PGMEA (480.0) | 40 | 0.15 | 25 | 3.0 | good |
| 4 | Polyimer1 (80.0) | PAG5 (3.0) | — | TBA (0.1) | PGMEA (480.0) | 45 | 0.15 | 23 | 3.0 | good |
| 5 | Polymer1 (80.0) | PAG1 (1.5) PAG2 (1.5) | — | TBA (0.1) | PGMEA (480.0) | 35 | 0.15 | 23 | 3.0 | good |
| 6 | Polymer1 (80.0) | PAG3 (1.5) PAG4 (1.5) | — | TEA (0.1) | PGMEA (480.0) | 35 | 0.15 | 30 | 2.5 | good |
| 7 | Polymer2 (80.0) | PAG3 (1.5) PAG6 (2.0) | — | TBA (0.1) | PGMEA (480.0) | 38 | 0.15 | 21 | 4.0 | good |
| 8 | Polymer3 (80.0) | PAG3 (2.0) PAG7 (1.0) | — | TBA (0.1) | PGMEA (480.0) | 30 | 0.15 | 23 | 4.0 | good |
| 9 | Polymer4 (80.0) | PAG1 (1.5) PAG4 (1.0) | — | TBA (0.1) | PGMEA (480.0) | 33 | 0.15 | 20 | 7.0 | good |
| 10 | Polymer5 (80.0) | PAG5 (3.0) | — | TBA (0.1) | PGMEA (480.0) | 40 | 0.16 | 22 | 5.0 | good |

TABLE 1-continued

| Example | Resin (pbw) | Photoacid generator (pbw) | Dissolution inhibitor or organic acid derivative (pbw) | Basic compound (pbw) | Solvent (pbw) | Eop (mJ/cm$^2$) | Resolution (μm) | I/G bias (nm) | Line edge roughness (nm) | Storage stability after 100 days |
|---|---|---|---|---|---|---|---|---|---|---|
| 11 | Polymer6 (80.0) | PAG1 (3.0) | — | TBA (0.1) | PGMEA (480.0) | 28 | 0.15 | 20 | 3.0 | good |
| 12 | Polymer7 (80.0) | PAG3 (3.0) | — | TBA (0.1) | PGMEA (480.0) | 35 | 0.15 | 40 | 6.0 | good |
| 13 | Polymer8 (80.0) | PAG1 (3.0) | — | TBA (0.1) | PGMEA (480.0) | 30 | 0.15 | 35 | 6.0 | good |
| 14 | Polymer9 (80.0) | PAG3 (3.0) | ACC1 (0.5) | TBA (0.1) | CyHO (480.0) | 28 | 0.15 | 35 | 4.5 | good |
| 15 | Polymer10 (80.0) | PAG1 (3.0) | — | TBA (0.1) | CyHO (480.0) | 28 | 0.15 | 40 | 3.5 | good |
| 16 | Polymer11 (80.0) | PAG3 (3.0) | — | TBA (0.1) | CyHO (480.0) | 25 | 0.18 | 40 | 3.5 | good |
| 17 | Polymer12 (80.0) | PAG1 (3.0) | ACC2 (0.3) | TBA (0.1) | PGMEA (480.0) | 22 | 0.15 | 30 | 9.0 | good |
| 18 | Polymer13 (80.0) | PAG3 (3.0) | — | TBA (0.1) | CyHO (480.0) | 35 | 0.18 | 40 | 3.0 | good |
| 19 | Polymer14 (80.0) | PAG1 (3.0) | — | TBA (0.1) | CyHO (480.0) | 22 | 0.18 | 40 | 5.0 | good |
| 20 | Polymer15 (80.0) | PAG1 (3.0) | DRR1 (2.0) | TBA (0.1) | CyHO (480.0) | 26 | 0.16 | 45 | 6.0 | good |
| 21 | Polymer16 (80.0) | PAG3 (3.0) | DRR2 (2.0) | TBA (0.1) | PGMEA (480.0) | 34 | 0.16 | 40 | 4.0 | good |
| 22 | Polymer17 (80.0) | PAG1 (3.0) | — | TBA (0.1) | PGMEA (480.0) | 38 | 0.16 | 40 | 6.0 | good |
| 23 | Polymer18 (80.0) | PAG1 (3.0) | DRR3 (2.0) | AAA (0.18) | PGMEA (480.0) | 32 | 0.16 | 20 | 7.0 | good |
| 24 | Polymer19 (80.0) | PAG3 (3.0) | DRR4 (2.0) | TEA (0.1) | PGMEA (480.0) | 34 | 0.17 | 25 | 5.0 | good |
| 25 | Polymer20 (80.0) | PAG1 (3.0) | — | AACN (0.16) | PGMEA (480.0) | 28 | 0.18 | 30 | 3.0 | good |
| 26 | Polymer7 (40) Polymer10 (40) | PAG3 (3.0) | — | TBA (0.1) | CyHO (480.0) | 35 | 0.15 | 30 | 3.0 | good |
| 27 | Polymer7 (40) Polymer11 (40) | PAG3 (2.0) PAG7 (1.0) | — | TEA (0.1) | CyHO (480.0) | 30 | 0.15 | 35 | 3.0 | good |

TABLE 2

| Example | Resin (pbw) | Photoacid generator (pbw) | Dissolution inhibitor or organic acid derivative (pbw) | Basic compound (pbw) | Solvent (pbw) | Eop (mJ/cm$^2$) | Resolution (μm) | I/G bias (nm) | Line edge roughness (nm) | Storage stability after 100 days |
|---|---|---|---|---|---|---|---|---|---|---|
| 28 | Polymer21 (80.0) | PAG1 (3.0) | — | TMMEA (0.1) | PGMEA (560.0) | 55 | 0.15 | 21 | 5.0 | good |
| 29 | Polymer21 (80.0) | PAG2 (3.0) | — | TMMEA (0.1) | PGMEA (560.0) | 65 | 0.16 | 23 | 5.0 | good |
| 30 | Polymer21 (80.0) | PAG3 (3.0) | — | TMMEA (0.1) | PGMEA (560.0) | 45 | 0.15 | 20 | 4.5 | good |
| 31 | Polymer21 (80.0) | PAG5 (3.0) | — | TMMEA (0.1) | PGMEA (560.0) | 50 | 0.15 | 22 | 5.0 | good |
| 32 | Polymer21 (80.0) | PAG1 (2.0) PAG7 (2.0) | — | TMMEA (0.1) | PGMEA (560.0) | 50 | 0.15 | 20 | 6.0 | good |
| 33 | Polymer21 (80.0) | PAG4 (1.0) PAG8 (2.0) | — | AAA (0.1) | PG/EL (560.0) | 55 | 0.16 | 21 | 4.0 | good |
| 34 | Polymer22 (80.0) | PAG3 (2.0) PAG7 (1.0) | — | TMMEA (0.1) | PGMEA (560.0) | 60 | 0.15 | 23 | 4.0 | good |
| 35 | Polymer23 (80.0) | PAG3 (1.5) PAG9 (1.0) | — | TMMEA (0.1) | PGMEA (560.0) | 45 | 0.15 | 20 | 5.5 | good |
| 36 | Polymer22 (80.0) | PAG3 (2.0) PAG8 (2.0) | — | TMMEA (0.1) | PGMEA (560.0) | 50 | 0.15 | 22 | 4.0 | good |
| 37 | Polymer22 (80.0) | PAG2 (1.0) PAG10 (2.0) | — | TMMEA (0.1) | PGMEA (560.0) | 45 | 0.16 | 20 | 5.0 | good |

TABLE 2-continued

| Example | Resin (pbw) | Photoacid generator (pbw) | Dissolution inhibitor or organic acid derivative (pbw) | Basic compound (pbw) | Solvent (pbw) | Eop (mJ/cm$^2$) | Resolution (μm) | I/G bias (nm) | Line edge roughness (nm) | Storage stability after 100 days |
|---|---|---|---|---|---|---|---|---|---|---|
| 38 | Polymer22 (80.0) | PAG3 (1.0) PAG7 (2.0) | — | TMMEA (0.1) | PGMEA (560.0) | 50 | 0.15 | 20 | 3.0 | good |
| 39 | Polymer22 (80.0) | PAG1 (1.0) PAG9 (2.0) | — | TMMEA (0.1) | PGMEA (560.0) | 50 | 0.15 | 30 | 6.0 | good |
| 40 | Polymer22 (80.0) | PAG4 (1.0) PAG10 (2.0) | — | TEA (0.1) | PGMEA (560.0) | 55 | 0.15 | 35 | 6.0 | good |

TABLE 3

| Comparative Example | Resin (pbw) | Photoacid generator (pbw) | Dissolution inhibitor or organic acid derivative (pbw) | Basic compound (pbw) | Solvent (pbw) | Eop (mJ/cm$^2$) | Resolution (μm) | I/G bias (nm) | Line edge roughness (nm) | Storage stability after 100 days |
|---|---|---|---|---|---|---|---|---|---|---|
| 1 | Polymer1 (80.0) | PAG6 (3.0) | — | TBA (0.1) | PGMEA (480.0) | 29 | 0.16 | 56 | 3.8 | good |
| 2 | Polymer1 (80.0) | PAG7 (3.0) | — | TBA (0.1) | PGMEA (480.0) | 25 | 0.18 | 65 | 4.5 | good |
| 3 | Polymer1 (80.0) | PAG11 (3.0) | — | TBA (0.1) | PGMEA (480.0) | 27 | 0.18 | 60 | 5.0 | poor, sensitivity drop |
| 4 | Polymer1 (80.0) | PAG12 (3.0) | — | TBA (0.1) | PGMEA (480.0) | 35 | 0.18 | 55 | 5.0 | poor, sensitivity drop |
| 5 | Polymer1 (80.0) | PAG13 (3.0) | — | TBA (0.1) | PGMEA (480.0) | 40 | 0.16 | 45 | 6.0 | poor, sensitivity drop |
| 6 | Polymer1 (80.0) | PAG7 (1.5) PAG13 (1.5) | — | TBA (0.1) | PG/EL (480.0) | 30 | 0.16 | 50 | 4.0 | poor, sensitivity drop |

It is evident from Tables 1 to 3 that the resist compositions within the scope of the invention have a higher sensitivity and resolution than the prior art resist compositions and are improved in line edge roughness and I/G bias.

All the aforementioned patent publications are incorporated herein by reference.

Japanese Patent Application No. 2003-132523 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A photoacid generator for chemically amplified resist compositions, having the following general formula (1b):

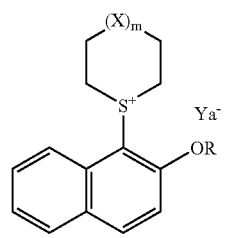

wherein R is hydrogen or a substituted or unsubstituted alkyl group of 1 to 10 carbon atoms, Ya$^-$ is a perfluoroalkylsulfonate of 1 to 8 carbon atoms, bis(perfluoroalkylsulfonyl)imide of 2 to 10 carbon atoms or tris(perfluoroalkylsulfonyl)methide of 3 to 12 carbon atoms, X is CH$_2$ (methylene) or O (oxygen atom), and m is 0 or 1.

2. A chemically amplified resist composition comprising
(A) a resin which changes its solubility in an alkaline developer under the action of an acid, and
(B) the photoacid generator of claim 1.

3. The resist composition of claim 2, further comprising (C) a compound capable of generating an acid upon exposure to radiation, other than component (B).

4. The resist composition of claim 2, wherein the resin (A) has such substituent groups having C—O—C linkages that the solubility in an alkaline developer changes as a result of scission of the C—O—C linkages under the action of an acid.

5. The resist composition of claim 2, further comprising (D) a basic compound.

6. A process for forming a pattern, comprising the steps of:
applying the resist composition of claim 2 onto a substrate to form a coating,
heat treating the coating and exposing the coating to high energy radiation with a wavelength of up to 250 nm or electron beam through a photomask,
optionally heat treating the exposed coating, and developing the coating with a developer.

7. A chemically amplified positive resist composition comprising
(A) a resin which changes its solubility in an alkaline developer under the action of an acid, and
(B) the photoacid generator of claim 1.

8. The photoacid generator of claim 1, wherein the cation skeletons of the sulfonium salts having formula (1b) are selected from the group consisting of:

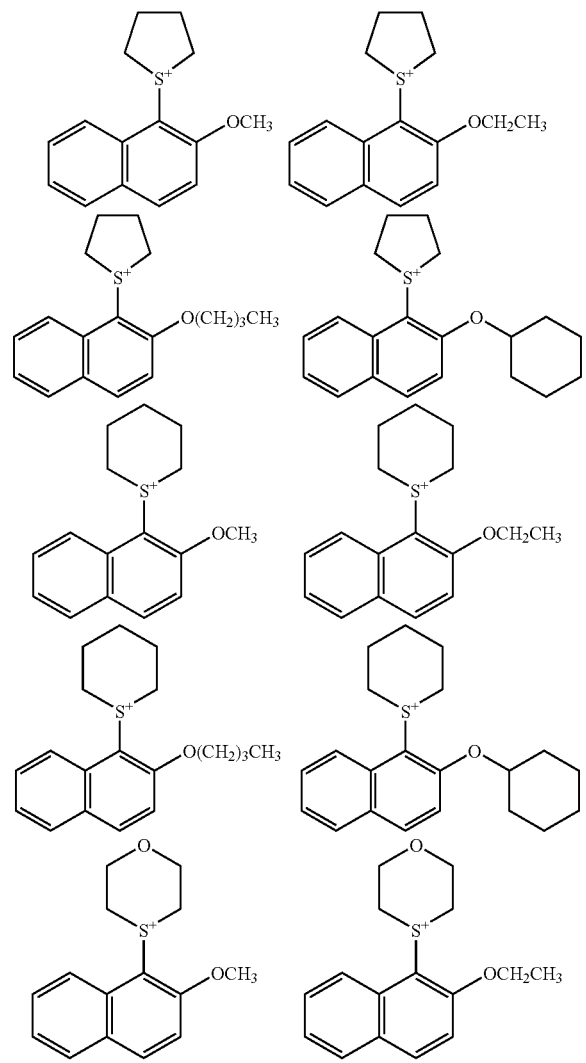

-continued

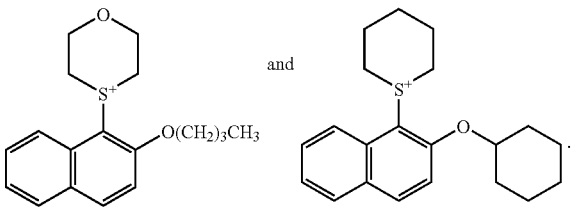

9. A chemically amplified resist composition comprising:
(A) a resin which changes its solubility in an alkaline developer under the action of an acid,
(B) a photoacid generator having the following general Formula (1):

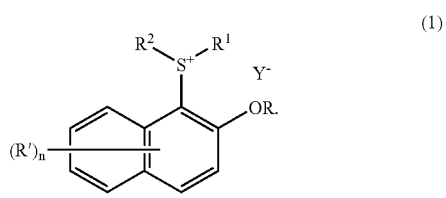

wherein $R^1$ and $R^2$ are each independently a straight, branched or cyclic, unsubstituted or oxygen-containing alkyl group of 1 to 6 carbon atoms, or $R^1$ and $R^2$, taken together, may form an unsubstituted or oxygen-containing ring structure of 4 to 6 carbon atoms with the sulfur atom to which they are attached,
R is hydrogen or a substituted or unsubstituted alkyl group of 1 to 10 carbon atoms,
R' is hydrogen, a substituted or unsubstituted alkyl group of 1 to 10 carbon atoms, a substituted or unsubstituted alkoxyl group of 1 to 10 carbon atoms, or a nitro group,
n is an integer of 1 to 6, and
$Y^-$ is a substituted or unsubstituted alkylsulfonate of 1 to 10 carbon atoms, a substituted or unsubstituted arylsulfonate of 6 to 20 carbon atoms, a substituted or unsubstituted bisalkylsulfonylimide of 2 to 10 carbon atoms, or a substituted or unsubstituted trisalkylsulfonylmethide of 3 to 12 carbon atoms, and
(C) a compound capable of generating an acid upon exposure to radiation, other than compound (B).

10. The resist composition of claim 9, further comprising (D) a basic compound.

11. A process for forming a pattern, comprising the steps of:
applying the resist composition of claim 9 onto a substrate to form a coating,
heat treating the coating and exposing the coating to high energy radiation with a wavelength of up to 250 nm or electron beam through a photomask,
optionally heat treating the exposed coating, and
developing the coating with a developer.

12. A chemically amplified resist composition comprising:
(A) a resin which changes its solubility in an alkaline developer under the action of an acid,
(B) a photoacid generator having the following general Formula (1a):

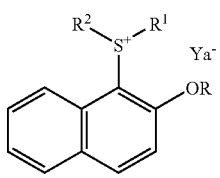

(1a)

wherein $R^1$ and $R^2$ are each independently a straight, branched or cyclic, unsubstituted or oxygen-containing alkyl group of 1 to 6 carbon atoms, or $R^1$ and $R^2$, taken together, may form an unsubstituted or oxygen-containing ring structure of 4 to 6 carbon atoms with the sulfur atom to which they are attached, R is hydrogen or a substituted or unsubstituted alkyl group of 1 to 10 carbon atoms, and $Ya^-$ is a perfluoroalkylsulfonate of 1 to 8 carbon atoms, bis(perfluoroalkylsulfonyl)imide of 2 to 20 carbon atoms, or tris(perfluoroalkylsulfonyl)methide of 3 to 12 carbon atoms, and (C) a compound capable of generating an acid upon exposure to radiation, other than compound (B).

13. A chemically amplified resist composition comprising:

(A) a resin having substituent groups having C—O—C linkages such that the solubility in an alkaline developer changes as a result of scission of the C—O—C linkages under the action of an acid, and (B) a photoacid generator having the following general Formula (1):

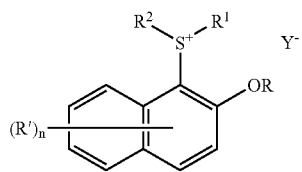

(1)

wherein $R^1$ and $R^2$ are each independently a straight, branched or cyclic, unsubstituted or oxygen-containing alkyl group of 1 to 6 carbon atoms, or $R^1$ and $R^2$, taken together, may form an unsubstituted or oxygen-containing ring structure of 4 to 6 carbon atoms with the sulfur atom to which they are attached, R is hydrogen or a substituted or unsubstituted alkyl group of 1 to 10 carbon atoms, R' is hydrogen, a substituted or unsubstituted alkyl group of 1 to 10 carbon atoms, a substituted or unsubstituted alkoxyl group of 1 to 10 carbon atoms, or a nitro group, n is an integer of 1 to 6, and $Y^-$ is a substituted or unsubstituted alkylsulfonate of 1 to 10 carbon atoms, a substituted or insubstituted arylsulfonate of 6 to 20 carbon atoms, a substituted or unsubstituted bisalkylsulfonylimide of 2 to 10 carbon atoms, or a substituted or unsubstituted trisalkylsulfonylmethide of 3 to 12 carbon atoms.

14. The resist composition of claim 13, further comprising (D) a basic compound.

15. A process for forming a pattern, comprising the steps of:

applying the resist composition of claim 13 onto a substrate to form a coating, heat treating the coating and exposing the coating to high energy radiation with a wavelength of up to 250 nm or electron beam through a photomask, optionally heat treating the exposed coating, and developing the coating with a developer.

16. A chemically amplified resist composition comprising:

(A) a resin having substituent groups having C—O—C linkages such that the solubility in an alkaline developer changes as a results of scission of the C—O—C linkages under the action of an acid, (B) a photoacid generator having the following general Formula (1a):

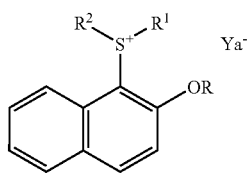

(1a)

wherein $R^1$ and $R^2$ are each independently a straight, branched or cyclic, unsubstituted or oxygen-containing alkyl group of 1 to 6 carbon atoms, or $R^1$ and $R^2$, taken together, may form an unsubstituted or oxygen-containing ring structure of 4 to 6 carbon atoms with the sulfur atom to which they are attached, R is hydrogen or a substituted or unsubstituted alkyl group of 1 to 10 carbon atoms, and $Ya^-$ is a perfluoroalkylsulfonate of 1 to 8 carbon atoms, bis(perfluoroalkylsulfonyl)imide of 2 to 20 carbon atoms, or tris(perfluoroalkylsulfonyl)methide of 3 to 12 carbon atoms.

* * * * *